US006774222B1

(12) United States Patent
Schneider et al.

(10) Patent No.: US 6,774,222 B1
(45) Date of Patent: Aug. 10, 2004

(54) MOLECULAR COMPUTING ELEMENTS, GATES AND FLIP-FLOPS

(75) Inventors: Thomas Schneider, Frederick, MD (US); Paul N. Hengen, Alameda, CA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/601,561
(22) PCT Filed: Feb. 17, 1999
(86) PCT No.: PCT/US99/03469
§ 371 (c)(1),
(2), (4) Date: Dec. 15, 2000
(87) PCT Pub. No.: WO99/42929
PCT Pub. Date: Aug. 26, 1999

Related U.S. Application Data
(60) Provisional application No. 60/075,468, filed on Feb. 20, 1998.

(51) Int. Cl.[7] ........................... C12Q 1/68; C12P 21/06; C07H 21/02; C07K 1/00
(52) U.S. Cl. ..................... 536/23.1; 435/6; 435/69.1; 530/350; 536/24.1
(58) Field of Search .............................. 536/23.1, 24.1; 530/350; 435/6, 69.1

(56) References Cited

U.S. PATENT DOCUMENTS 5,677,131 A * 10/1997 Wickens et al. ............... 435/6

OTHER PUBLICATIONS

Darnell et al. Eds. Molecular Cell Biology, published by Scientific American Books, 1990.*
Hengen et al. Nucleic Acids Research, 1997, vol. 25, No. 24, pp. 4997–5002.*
Aldeman, Leonard, M. "Molecular Computation of Solutions to Combinatorial Problems" Science 11/94 vol. 266 pp. 1021–1024.
Ashkenazi, et al. "A Molecular Switch for Biochemical Logic Gates: Conformational Studies" (1997) vol. 12 (2) pp. 85–95.
Barrick, et al. "Quantitative Analysis of Ribosome Binding Sites in *E.coli*" Nucleic Acids Research (1994) vol. 22 (7) pp. 1287–1295.
Ebina, et al. "LexA Protein is a Repressor of the Colicin E1 Gene" *J. of Biological Chemistry* 11/83 vol. 258 (21) pp. 13258–13261.
Gille, et al. "The FIS Protein Binds and Bends the Origin of the Chromosomal DNA Replication, oriC, of *Escherichia coli*" Nucleic Acids Research (1991) vol. 19 (15) pp. 4167–4172.

Heath, et al. "A Defect–Tolerant Computer Architecture: Opportunities for Nanotechnology" *Science Magazine* vol. 280 (5370) pp. 1716.
Hengen, et al. "Information Analysis of Fis Binding Sites" *Nucleic Acids Research* (1997) vol. 25 (24) pp. 4994–5002.
Johnson, et al "Interactions Between DNA–bound Repressors Govern Regulation by the λ Phage Repressor" *Proc. Natl. Acad Sci.* 10/79 vol. 76 (10) pp. 5061–5065.
Lu, et al. "Two Overlapping SOS–boxes in ColE Operons are Responsible for the Viability of Cells Harboring the Col Plasmid" *Mol. Gen. Genet* (1996) 251 pp. 407–411.
Messer, et al. "The Complex of oriC DNA with the DnaA Intiator Protein" *Res. Microbiol.* (1991) vol. 142 pp. 119–125.
Schlief, Robert "Molecular Recognition: Feeling for the Bumps" *Nature* 01/87 vol. 325 pp. 14–15.
Schneider, Thomas, D. "Information Content of Individual Genetic Sequences" *J. Theor. Biol.* (1997) vol. 189 pp. 427–441.
Schneider, Thomas, D. "Reading of DNA Sequence Logos: Prediction of Major Groove Binding by Information Theory" *Methods in Enzymology* vol. 274 pp. 445–455, 1996.
Schneider, Thomas, D. "Sequence Logos, Machine/channel Capacity, Maxwell's Demon, and Molecular Computers: a Review of the Theory of Molecular Machines" *Nanotechnology* 01/94 vol. 5 (1) pp. 1–18.
Schneider, Thomas, D. "Sequence Logos: A New Way to Display Consensus Sequences" *Nucleic Acids Research* 09/90 vol. 18 (20) pp. 6097–6100.
Schneider, Thomas, D. "Seqeucne Walkers: A Graphical Method to Display how Binding Proteins Interact with DNA or RNA Sequences" *Nucleic Acids Research* (1997) vol. 25 (21) pp. 4408–4415.
Schneider, Thomas, D. "Theory of Molecular Machines. II. Energy Dissipation from Molecular Machine" *J. Theor. Biol.* (1991) vol. 148 pp. 125–137.
Watson, J. "Recombinant DNA A Short Course" *Scientific American Books* (1983) pp. 46–53.
Yuh, et al. "Genomic Cis–Regulatory Logic: Experimental and Computational ANalysis of a Sea Urchin Gene" *Science* 03/98 vol. 279 pp. 1896–1902.

* cited by examiner

*Primary Examiner*—John Brusca
*Assistant Examiner*—Shubo (Joe) Zhou
(74) *Attorney, Agent, or Firm*—Townsend and Townsend and Crew LLP

(57) ABSTRACT

This invention relates to novel molecular constructs that act as various logic elements, i.e., gates and flip-flops. The constructs are useful in a wide variety of contexts including, but not limited to, computation and control systems. The basic functional unit of the construct comprises a nucleic acid having at least two protein binding sites that cannot be simultaneously occupied by their cognate binding protein. This basic unit can be assembled in any number of formats providing molecular constructs that act like traditional digital logic elements (flips-flops, gates, inverters, etc.).

65 Claims, 11 Drawing Sheets

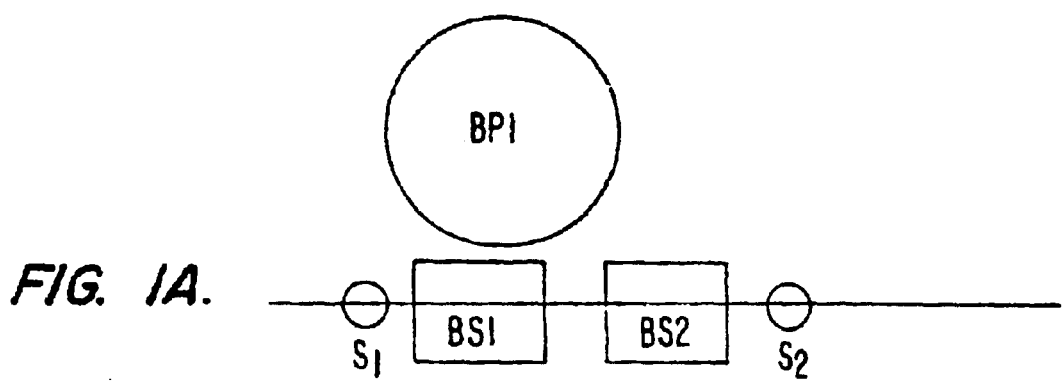
FIG. IA.
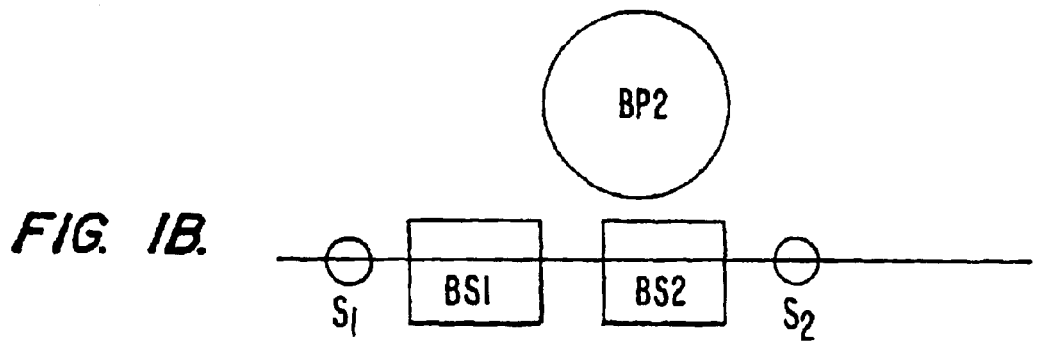
FIG. IB.

a) Overlap 11

5' tattcctttgctcaaaatttgatcaaatttgagcaaagaata 3'

FIG. 8a.

b) Overlap 7

5' aggctttgctcaaagtttaaacttttgagcaaagcct 3'

FIG. 8b.

c) S parat d 23

5' ggaattcttgctcaaattgatcaggatcctgaaatttgagcaaagaattcc 3'
   [------] EcoRI          [------] BamHI          [------] EcoRI

MOLECULAR COMPUTING ELEMENTS, GATES AND FLIP-FLOPS

CROSS-REFERENCE TO RELATED APPLICATIONS

This application claims the benefit of provisional application No. 60/075,468, filed Feb. 20, 1998.

STATEMENT AS TO RIGHTS TO INVENTIONS MADE UNDER FEDERALLY SPONSORED RESEARCH AND DEVELOPMENT

[Not Applicable]

FIELD OF THE INVENTION

This invention relates to novel molecular constructs that act as various logic elements, i.e., gates and flip-flops. The constructs are useful in a wide variety of contexts including, but not limited to, computation and control systems.

BACKGROUND OF THE INVENTION

The history of computational devices reveals a progression from larger and slower to smaller and faster devices. Huge stepwise advances in this progression have accompanied significant changes in the underlying technology. Thus, for example, vast increases in computational speed accompanied the transition from mechanical, hand-operated devices such as the abacus and hand operated cash-register or calculator to electrically driven mechanical computers (e.g., the electric cash register/calculator). Similarly significant increases in speed and decreases in size accompanied the shift from mechanical based devices to tube-based electronic computers, again with the shift from tube-based electronic computers to transistor-based electronic computers, and yet again with the shift from discrete transistor circuits to integrated circuits to large scale integrated (LSI) circuits.

The continually decreasing size and increasing speed of large scale integrated electronic devices has recently provoked increased interest and concern regarding the theoretical and practical limits of this progression. Such theoretical limits are affected by the inherent noise in electronic systems, the need to dissipate heat across ever decreasing surface areas as the feature size of various elements decreases, and the "anomalous" behavior of devices as their physical size decreases to a point at which quantum mechanical rather than macroscopic properties predominate. (It will be noted however, that the emergence of quantum mechanical properties at small feature size may provide the basis for quantum computing devices and this field is receiving considerable interest). Practical limits are imposed by costs and difficulties in predictable and reliable microfabrication.

Another approach to the improvement in computational power and/or efficiency has involved the substitution of "linear" computing systems in which a single processor sequentially performs the necessary operations in a calculation with "parallel" computing system in which components of each calculation are distributed across two or more processing elements. Parallel computing systems can achieve vast savings in computational time. For example, an algorithm running on 100 computing elements in parallel in principle can run about 100 times faster than the same algorithm on a single element that must process each operation sequentially. Of course the actual gain in efficiency is less than 100 because some time is lost in parsing the algorithm between the various computing elements, in integrating the elements, and because some elements may have to wait for other elements to complete their calculation before the next operation can proceed. Nevertheless, massively parallel systems have been able to solve problems (e.g., identify large prime numbers) that could not be practically determined on linear computer systems.

A combination of the two approaches, massive parallelism combined with small computational element size has birthed the field of molecular computing. This is illustrated in the seminal paper by Adleman (1994) Science 266: 1021–1024, in which molecular biological tools were used to solve an instance of the directed Hamiltonian path problem. In particular, Adleman encoded the problem (a directed Graph) into nucleic acid sequences and then performed a series of ligations that ultimately produced an encoded solution which could then be decoded. Following Schneider (1991) J. Theoret. Biol., 148: 125, Adleman suggested that such molecular systems could demonstrate remarkable energy efficiency with a theoretical maximum of $34 \times 10^{19}$ operations per Joule while conventional supercomputers execute at most $10^9$ operations per joule.

Adleman recognized that DNA molecular computing imposed certain difficulty and limitations, particularly on the encoding of various problems and recognized that conventional electronic computers have an advantage in the variety of operations they provide and the flexibility with which these operations can be applied. He did, however, note that for certain intrinsically complex problems, such as the directed Hamiltonian path problem where existing electronic computers are very inefficient and where massively parallel searches can be organized to take advantages of the operations provided by molecular biology, such molecular computations may be advantageous.

As indicated by Adleman, one limitation of prior molecular computation systems has been the lack of a variety of operations and the flexibility with which they may be applied.

SUMMARY OF THE INVENTION

This invention overcomes a number of these limitations by providing molecular logic devices that operate in a manner analogous to their electronic counterparts and thus provide a wide variety of operations. Thus, in one embodiment, this invention provides molecular bistable elements (flip-flops) and a wide variety of logic elements (gates) such as the AND, OR, NAND, NOR, NOT gates and others.

The central operational element of these devices is a nucleic acid having two or more protein binding sites (e.g., a first protein binding site and a second protein binding site). The sites are arranged such that when the first protein binding site is specifically bound by a protein, the second binding site cannot be bound by a protein that otherwise specifically recognizes and binds the second binding site; and when the second binding site is specifically bound by a protein, the first binding site cannot be bound by a protein that otherwise specifically recognizes and binds the first binding site. The binding sites are thus mutually exclusive. The nucleic acid can be a single or double stranded nucleic acid, however double stranded nucleic acids (e.g., DNA) are preferred. The first and the second binding sites can have the same or different nucleotide sequences. In one preferred embodiment the first and second binding sites are the same and have the nucleotide sequence of SEQ ID NO: 1 described herein.

The binding sites can be chosen so that they are specifically recognized (bound) by any of the nucleic acid binding proteins described herein (e.g., Fis, modified EF-tu, Tus, and LexA).

As indicated above, the binding sites are spaced so that they are mutually exclusive (only one can be bound at a time). The first binding site is preferably within 20 nucleotides (base pairs) of the second site, more preferably within 15 base pairs, and most preferably within 11 or fewer base pairs of the second site. Preferred binding sites have a strength of at least 2.4 bits as determined by individual information theory. The difference in strength between the two sites is at least 0 bits as determined by individual information theory.

The "flip-flop" may additionally include one or more selector binding sites (e.g. a third protein binding site) where the selector binding site is in proximity to the first protein binding site or to the second protein binding site such that specific binding of the third binding site (e.g., with a protein) precludes specific protein binding of the first or second protein binding sites.

In one preferred embodiment the flip-flop comprises the above-described nucleic acid in which the first protein binding site is a Fis binding site; the second protein binding site is a Fis binding site; and the binding sites are separated from each other by less a than 12 nucleotide base pairs. In a particularly preferred flip-flop the nucleic acid is a deoxyribonucleic acid comprising the sequence of SEQ ID NO: 2 or SEQ ID NO: 3 described herein.

In another embodiment this invention provides the various logic gates (NOR, OR, NOT, AND, NAND) described herein. The fundamental unit of these gates is the NOR gate. In one embodiment, the NOR gate is a composition comprising an isolated nucleic acid having a length of at least 5 base pairs and having a nucleotide sequence that encodes a first protein binding site, a second protein binding site, and a third protein binding site where the protein binding sites are spaced in proximity to each other such that when either the first protein binding site or the third protein binding is specifically bound by a nucleic acid binding protein, the second binding site cannot be bound by a nucleic acid binding protein that otherwise specifically recognizes and binds the second binding site; and where the first protein binding site and the third protein binding site can simultaneously be specifically bound by a nucleic acid binding protein. The NOR gate can be in a state in which the first or third binding site is bound by a nucleic acid binding protein (e.g. Fis or any of the binding proteins described herein) and thus set in a HIGH state. Similarly, the second binding site can be bound by a nucleic acid binding protein, but not when either the first or the second site is bound.

The binding protein bound to the second binding site can be attached to an activator (e.g. a gene transactivator such as Gal4). In addition, the NOR gate can further comprise a gene or cDNA under the control of the activator. The gene or cDNA can encode virtually any structural protein. Thus, in one embodiment, the gene may be a reporter gene (e.g., FFlux, GFP, etc.) or in another embodiment the gene may encode a nucleic acid binding protein. This provides a method of coupling the output of one gate or flip-flop to the input of the same gate or flip-flop or to the input of another gate or flip-flop.

As with the flip-flop described above, in one embodiment, the underlying nucleic acid can be double stranded (e.g., a DNA). The three binding sites comprising the NOR gate can all be different (in which case, no selectors are necessary although they optionally can be present). Alternatively, the first and third binding sites can have the same nucleotide sequence (i.e., bind the same protein with the same strength) in which case, the NOR gate acts like a NOT gate (when $I_1=I_2$, $NOR(I_1,I_2)=NOT(I_1)$). In another embodiment, the first or third binding sites and the second binding site can have the same nucleotide sequence. The binding sites can be chosen so that they are cognate binding sites for any particular binding protein. Preferred spacings between the first and second site and between the second and third site are as described above.

Preferred binding sites have a binding strength of at least 2.4 bits as determined by individual information theory. In one embodiment, the difference in strength between the first, and third site is at least 0 bits as determined by individual information theory. In a particularly preferred embodiment, the first protein binding site is a Fis binding site; and the third protein binding site is a Fis binding site (e.g., the binding site of SEQ ID NO: 1)

In another embodiment this invention provides a composition for the storage of binary information. The preferred storage composition comprises any of the flip-flops described above having a nucleic acid binding protein bound to the first protein binding site or to the second protein binding site. The underlying nucleic acid can have restriction sites at one or both ends and preferably different restriction sites at each end. The restriction sites are preferably located so that when the binding site adjacent to a restriction site is occupied with a binding protein, a ligase is incapable of ligating the mating strand to that restriction site.

The storage composition can be free in solution or it can be attached to a solid support The binding protein may be covalently linked to the underlying nucleic acid. The binding protein can be attached to a gene transactivator as described above. In addition, the storage composition can include one or more genes or cDNAs as described above that are preferably under control of the activator.

In still another embodiment, this invention provides a method of storing information. The method involves binding a nucleic acid binding protein to a first protein binding site on a nucleic acid comprising any of the above-described flip-flops or on a nucleic acid comprising any of the gates described herein. The method may further involve the step of determining which binding site on the nucleic acid is bound by said binding protein.

This invention also provides a method of transforming binary information. This method involves binding a nucleic acid binding protein to an input protein binding site on any one or more of the gates described herein and determining whether or not a nucleic acid binding protein can bind to an output protein binding site. The output binding site can be on the same or a different gate and it can be on the same or a different nucleic acid. In a preferred embodiment, a nucleic acid comprising a gate used for this purpose has a length of at least 3, preferably a length of at least 5, more preferably a length of at least 7 and most preferably a length of at least 22 base pairs.

DEFINITIONS

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides. The term also includes nucleotides linked by peptide linkages as in "peptide" nucleic acids.

The term "specifically binds", as used herein, when referring to the binding of a protein or polypeptide to a nucleic acid refers to a protein nucleic acid interaction in which the protein binds strongly to a specific nucleic acid sequence pattern (nucleotide sequence) and less strongly to other different nucleic acid patterns (e.g., in a gel shift assay, specific binding will show an significant gel shift as compared to the gel shift shown by the same protein to other different nucleic acid sequences of the same length).

The term "nucleic acid binding protein" is used herein to refer to a protein that specifically binds to a nucleic acid at a particular nucleotide sequence. Nucleic acid binding proteins include DNA binding proteins, mRNA binding proteins, tRNA binding proteins, and proteins that specifically bind modified or otherwise non-standard nucleic acids as described above. Nucleic acid binding proteins include, but are not limited to DNA binding proteins such as Fis, LacI, lambda cI, lambda cro, LexA, TrpR, ArgR, AraC, CRP, FNR, OxyR, IHF, GalR, MAIT, LRP, SoxR, SoxS, sigma factors, chi, T4 MotA, P1 RepA, p53, NF-kappa-B, and RNA binding proteins or proteins/RNA complexes such as ribosomes, T4 regA, spliceosomes (donor and acceptor), polyA binding factor, and the like. A large number of nucleic acid binding proteins are described in the TransFac database, see also *Nucleic Acids Res*. (25)(1)265–268 (1997).

A "protein binding site" refers to a nucleotide sequence in a nucleic acid to which a particular nucleic acid binding protein specifically binds.

The terms "cognate protein" or "cognate binding site" refer to the protein that specifically binds to the binding site or to the binding site that is specifically bound by a particular binding protein, respectively.

A binding site "blocker", "selector", or "modulator" refers to a moiety that when bound adjacent to, in proximity to or on a binding site, partially or completely blocks binding of that site by its cognate nucleic acid binding protein.

The term "flip-flop" refers to a bistable device that exists-in one or the other of two mutually exclusive states. Thus the molecular flip-flops of this invention have two binding sites. only one of which can be bound at a time.

The term "gate" is used to refer to a device that produces a particular (predetermined) output in response to one or more inputs. Thus, for example, an AND gate produces a HIGH output only when all inputs are HIGH. An OR gate produces a HIGH output when any input is HIGH and a LOW output only when all inputs are LOW. A NOT function returns a HIGH when input is LOW and a LOW when input is HIGH. Gates and their uses are well known to those of skill in the art (see, e.g. Horowitz and Hill (1990) *The Art of Electronics*, Cambridge University Press, Cambridge).

The term "state" is used to refer to the signal state of a particular binding site of a flip-flop or of a logic gate of this invention. A protein binding site that is protein bound or capable of being protein bound is said to be HIGH, while a binding site that is unbound and cannot be bound by a binding protein is said to be LOW.

The term "input" is used herein to refer to a binding site to which a signal may be applied in order to elicit an output. The signal itself (e.g., a signal polypeptide) may also be referred to as an input. The difference will be determined from the context of usage. The term "input binding site" refers to a protein binding site that is used as an input.

The term "output" is used herein to refer to a binding site that is rendered capable or incapable of binding its cognate protein as a consequence of an input binding event or events. The term output can also refer to the state of the output binding site. The output can provide an input for another gate or flip-flop of this invention.

A "signal protein" is a nucleic acid binding protein that sets the (logical) state of a molecular flip-flop or of a molecular gate of this invention. As described herein, binding of a signal protein to a protein binding site on a nucleic acid sets the state of that binding site high. A signal protein can also be used to read the state of the flip-flop or gate. In this latter context, where the protein is capable of binding an output binding site (i.e., the binding site is unblocked), the state of the output is said to be HIGH. Conversely, where the output binding site is blocked, the state is said to be LOW.

The term "setting the state" when referring to a binding site refers to selectively binding or unbinding a signal protein from a particular binding site. Where the signal protein is bound to the binding site, the state of that binding site is set high. Conversely, where the signal protein is removed from the site, the state is set LOW. With respect to a flip-flop, setting the state refers to setting the flip-flop into one of its mutually exclusive stable states. Thus state one can be set by binding a signal protein to the first binding site, while state two can be set binding a signal protein to the second binding sites. Since the two states are mutually exclusive setting the state at one site implicitly involves setting (or switching) the state at the other site.

The term "resetting the state" the state refers to changing the state (e.g., from HIGH to LOW or from LOW to HIGH) of an input binding site, an output binding site, or a flip-flop.

The term "GTPase-like" protein refers to a binding protein that can release a bound nucleic acid with the dissipation of energy (e.g., hydrolysis of an energy source such as GTP, ATP, etc., or input of light). Such release may optionally be accomplished with the additional use of a co-factor. A GTPase-like protein includes naturally occurring GTPase-like proteins (including GTPases) as well as modified and non-natural GTPase-like proteins.

A "recombinant expression cassette" or simply an "expression cassette" is a nucleic acid construct, generated recombinantly or synthetically, with nucleic acid elements that are capable of affecting expression of a structural gene or genes in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell.

A "logic cassette" refers to an expression cassette in which the expression of one or more genes is under the control of one or more molecular gates or flip-flops of this invention.

The phrase "expression is under the control of" when referring to a logic element (e.g., gate or flip-flop) indicates that changes in the state(s) (input and/or output) of the gate or flip-flop alters the expression level of the gene or gene under said control.

Similarly, a gene "operably linked" or "under the control" of an activator refers to a gene whose expression is altered by the presence or absence of a particular activator.

A "tethered activator" refers to a gene activator (e.g. Ga14) bound directly or through a linker to a nucleic acid binding protein (e.g. LexA). The attachment can be chemical conjugation or by recombinant expression of a fusion protein. In some instances a repressor can be used in place of the activator and the tern tethered activator is intended to encompass this possibility.

The term "binding strength" as used herein refers to binding strength as calculated using individual information theory (e.g., as described in Schneider (1997) *J. Theoret. Biol.*, 189(4): 427–441) or as measured by binding energy ($-\Delta G$).

The terms "isolated" "purified" or "biologically pure" refer to material which is substantially or essentially free from components which normally accompany it as found in its native state. In the case of a nucleic acid, an isolated nucleic acid is typically free of the nucleic acid sequences by which it is flanked in nature. An isolated nucleic acid can be reintroduced into a cell and such "heterologous" nucleic acids are regarded herein as isolated. In addition, nucleic acids synthesized de novo or produced by cloning (e.g. recombinant DNA technology) are also regarded as "isolated".

The term "sequence logo" refers to-a graphical method for displaying the patterns in a set of aligned sequences. The characters representing the sequence are stacked on top of each other for each position in the aligned sequences. The height of each letter is proportional to its frequency and the letters are sorted so the most common is on top. The height of the entire stack is then adjusted to signify the information content of the sequences at that position. From these "sequence logos" one can determine not only the consensus sequence, but also the relative frequency of bases and information content (measured in bits) at every position in a site or sequence. The logo displays both significant residues and subtle sequence patterns. Sequence logos are described in detail in Schneider & Stephens (1990) *Nucl. Acids Res.*, 18: 6097–6100 and Schneider (1996) *Meth. Enzym.*, 274: 445–455.

The term "sequence walker" refers to a graphical method for displaying how binding proteins and other macromolecules interact with individual bases of nucleotide sequences. Characters representing the sequence are either oriented normally and placed above a line indicating favorable contact, or upside-down and placed below the line indicating unfavorable contact. The positive or negative height of each letter shows the contribution of that base to the average sequence conservation of the binding site, as represented by a sequence logo. These sequence "walkers" can be stepped along raw sequence data to visually search for binding sites. Many walkers, for the same or different proteins, can be simultaneously placed next to a sequence to create a quantitative map of a complex genetic region. One can alter the sequence to quantitatively engineer binding sites. Database anomalies can be visualized by placing a walker at the recorded positions of a binding molecule and by comparing this to locations found by scanning the nearby sequences. The sequence can also be altered to predict whether a change is a polymorphism or a mutation for the recognizer being modeled. The calculation and use of "sequence walkers" are described in Schneider (1997) *Nucl. Acids Res.*, 25: 4408–4415, and in copending application U.S. Ser. No. 08/494,115, filed on Jun. 23, 1995. The mathematics for walkers is given in: Schneider (1997) *J. Theor. Biol.* 189(4): 427–441

BRIEF DESCRIPTION OF THE DRAWINGS

FIGS. 1a and 1b illustrate the two states of a basic molecular flip-flop. The horizontal line represents a nucleic acid while the boxes labeled BS1 and BS2 represent protein binding sites. The circles, labeled BP1 and BP2 represent binding proteins that bind to BS1 and BS2 respectively. The binding sites are situated so that when BP1 is bound to BS1, BS2 cannot be occupied. Conversely when BP2 binds to BS2, BS1 cannot be occupied. BS1 and BS2 can be the same type of protein binding site or different kinds of protein binding sites (ie., bind different proteins). Similarly, BP1 and BP2 can be the same or different kinds of binding proteins. The circles $S_1$ and $S_2$ represent optional "selectors", binding sites that when bound block BS1 and BS2 and thereby allow selective setting of the state of the flip-flop.

In FIG. 3, the gene expresses a binding protein that can specifically bind to $I_3$ or $I_4$ of gate B thereby illustrating the coupling of the output of Gate A to the input of Gate B. The output of gate B ($O_2$) produces an OR in response to inputs ($I_1$ or $I_2$) at gate A. Any of the illustrated binding sites may also optionally occur with a selector molecule.

FIG. 6 shows a resettable flip-flop utilizing GTPase-like proteins. The flip-flop consists of a nucleic acid having 4 binding sites, designated c, $a_1$, b, and $a_2$. The site can be bound by $\sigma_x$ which is a nucleic acid binding protein. The a proteins are GTPase-like proteins that, when triggered, release the nuclei acid. The proteins also contain a GAP finger that can trigger the release of the adjacent σ protein, but that cannot trigger its own release. The $\sigma_c$ protein then binds site c and because of its GAP finger, causes the removal of a $\sigma_a$ at site $a_1$. Thus, when the flip-flop is contacted with $\sigma_a$ the $\sigma_a$ only remains bound at site a2. The flip-slop is thus stable at site $a_2$. To switch its state, the flip-flop is contacted with $\sigma_b$ that binds at site b causing the removal of $\sigma_a$ and leaving the flip-flop stably bound at site b, the second state of the flip-flop. The flip-flop can be reset to state a by contacting it with $\sigma_a$ which binds to sites $a_1$ and $a_2$. Site ax is bound long enough to cause the release of $\sigma_b$ before the $\sigma_a$ molecule is removed by $\sigma_c$. This leaves the flip-flop reset to state a, with site a2 bound by $\sigma_a$. The cycle can be repeated indefinitely.

Figure 7:
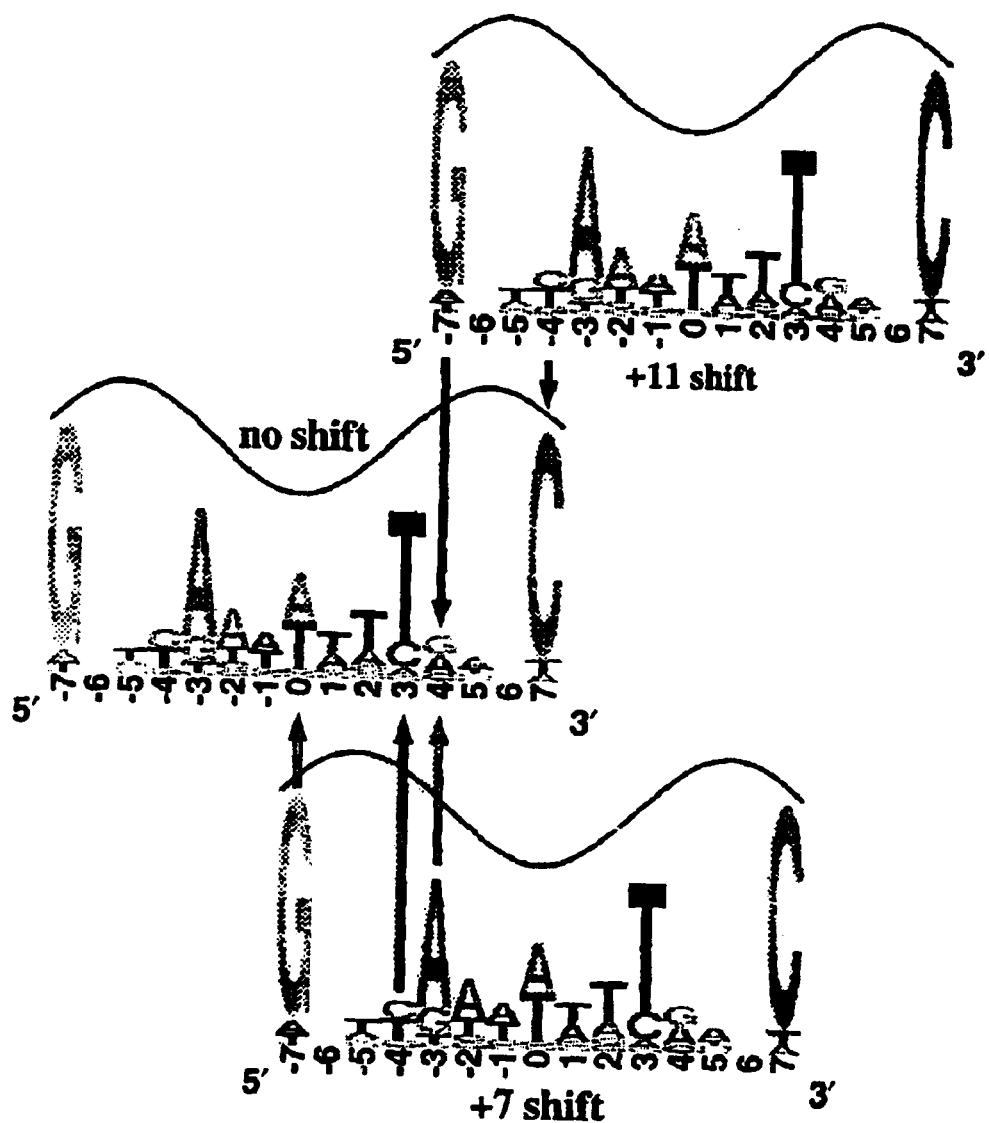

FIG. 7 illustrates the self-similarity of Fis binding sites. The sequence logo for Fis (SEQ ID NO:4) (Schneider & Stephens (1990) *Nucl. Acids Res.*, 18: 6097–6100; Hengen et al. (1997) *Nucl. Acids Res.*, 25(24): 4994–5002) is shown three times. The upper and lower logos, are shifted +11 and +7 bases to the right (respectively) relative to the middle logo. The cosine wave, with a wavelength of 10.6 bases, shows that the +11 relatively shifted Fis sites would be on the same face of the DNA, while the +7 relatively shifted Fis sites would be on opposite faces. Arrows are at positions where the logo is self-similar after a shift. Down arrows mean that the contacts by Fis to the bases would interfere because they would be on the same face of the DNA. Up arrows mean that the contacts could be simultaneous because they are on opposite faces.

FIGS. 8a, 8b, and 8c illustrate the oligonucleotide design of overlapping and separated Fis binding sites. The predicted Fis sites are shown by walkers floating below each DNA sequence (Schneider (1997) *Nucl. Acids Res.*, 25: 4408–4415; Hengen et al. (1997) supra). In a walker, the vertical box marks the zero base of the binding site. The box also shows the vertical scale, with the upper edge being at +2 bits and the lower edge being at −3 bits. The height of each letter is determined from the bit value in the Riw(b,1) matrix (Schneider (1997) *J. Theoret. Biol.*, 189(4): 427–441; Schneider (1997) *Nucl. Acids Res.*, 25: 4408–4415; Hengen et al. (1997) supra.). Negative weights are represented by drawing the letter upside-down and placing it below the zero bit level. Three DNAs were designed, each having two Fis sites spaced 11 (SEQ ID NO:2), 7 (SEQ ID NO:3) and 23 (SEQ ID NO:5) bases apart. Design details are given in Example 1, Materials and Methods. The total strength of a site is the sum of the information weights for each base. The 18.1 bit Fis sites (SEQ ID NOS: 6 and 7) are 3.4 standard deviations higher than the average Fis site in natural sequences (Hengen et al. (1997) supra.; Schneider (1997) *J. Theoret. Boo.*, 189(4):427–441). The 12.7 (SEQ ID NOS:8 and 9) and 15.0 (SEQ ID NOS:10 and I1) bit sites are 1.6 and 2.4 standard deviations above average (respectively).

Figure 9:
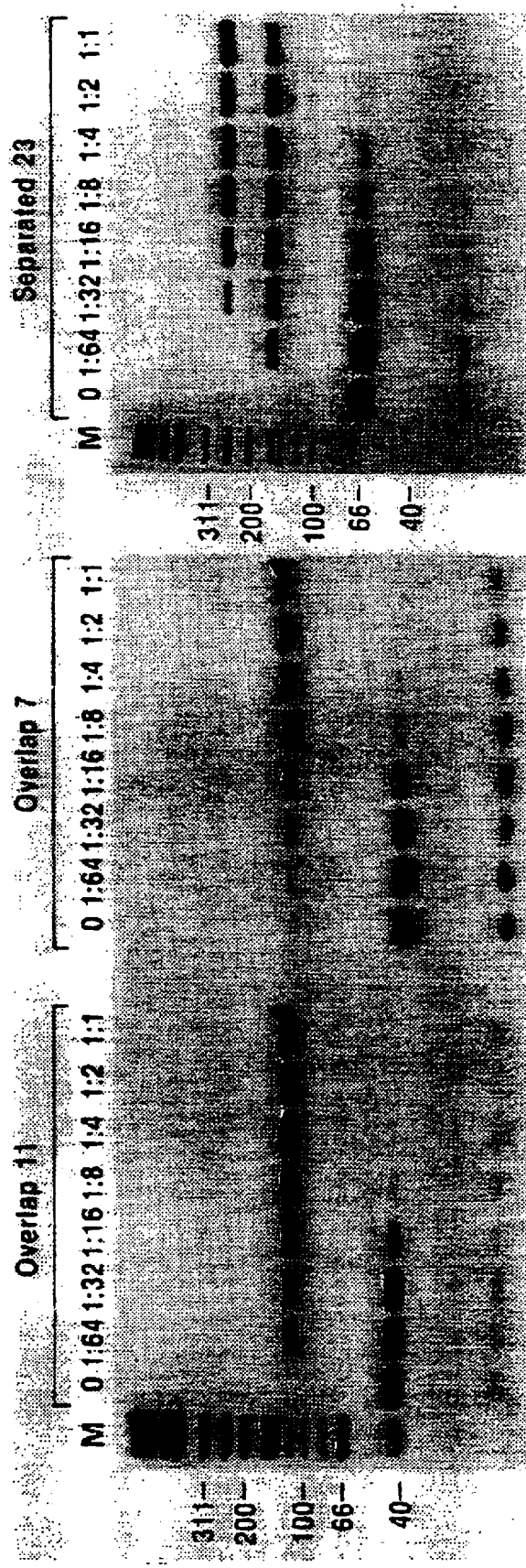

FIG. 9 illustrates the mobility shift experiments for 11 and 7 base pair overlapping and 23 base pair separated Fis sites. Each lane contains increasing concentrations of Fis protein, beginning with no Fis, Fis diluted 1 to 64, etc. The 1:1 dilution is at 2200 nM Fis. This concentration was chosen intentionally so that with 1 nM DNA per reaction, the protein/DNA ratio is 2-fold higher than that needed to strongly shift DNA containing the 8.9 bit wild-type hin distal Fis site (Bruist et al. (1987) *Genes Dev.* 1: 762–772). The sequences are given in FIG. 8. Marker lanes (M) contain 10 ng of biotinylated φX74 hinfI digested DNA standards (Life Technologies, Inc.). Sizes are indicated in bp. The lowest band in most lanes of the figure is single-stranded oligonucleotide DNA. In the "Separated 23" experiment, at high concentrations, Fis proteins are apparently able to capture the single-stranded DNA when it has folded into a hairpin. This produces a faint band near the 100 bp marker.

Figure 10:
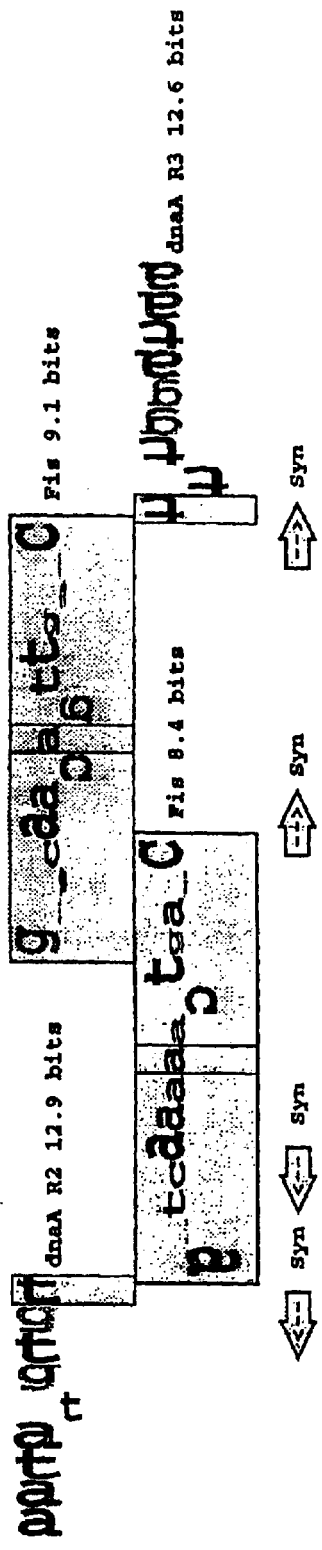

FIG. 10 shows the positions of Fis and DnaA sites at the *Escherichia coli* origin of replication (oriC). Sequence data are from GenBank accession K01789. The horizontal dashes below the sequence (SEQ ID NO:12) represent regions protected by Fis. Locations of DnaA sites are from Messer et al. (1991) *Res. Microbiol*, 142: 119–125). The asymmetric DnaA individual information matrix was created from 27 experimentally demonstrated DnaA binding sites (data not shown). DNA synthesis start sites are indicated by the arrows at the bottom (Seufert & Messer (1987) *EMBO J.* 6: 2469–2472). The boxes mark two Fis sites separated by 11 bases (SEQ ID NOS:13 and 14). Fis sites with positive individual information are marked from −7 to +7 but evaluated from −10 to +10 according to the matrix. DnaA site directionality is indicated by letters turned sideways in the direction that DnaA binds (Schneider (1997) *Nucl. Acids Res.*, 25: 4408–4415).

Figure 11:
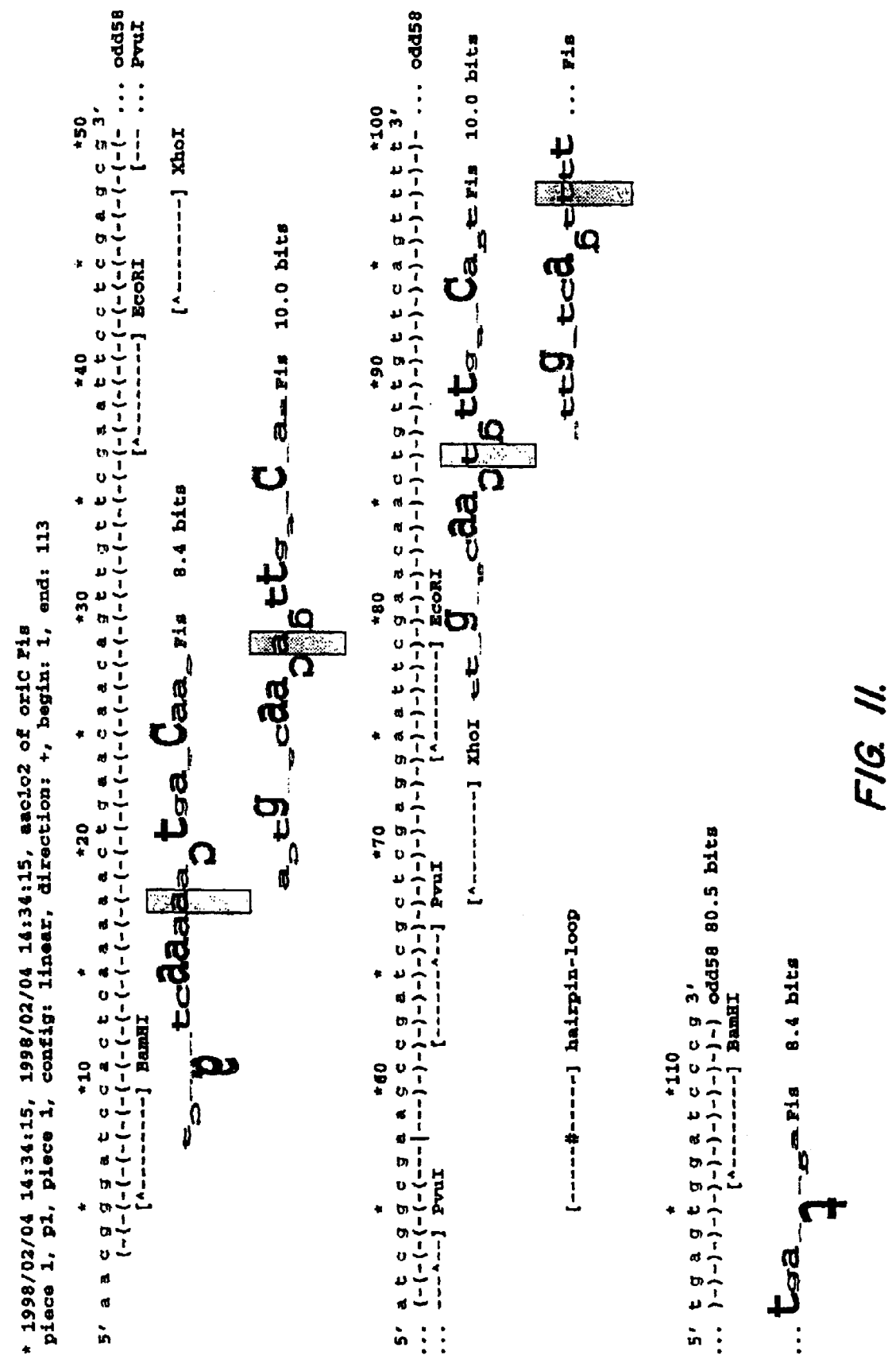

FIG. 11 shows the design of the oligonucleotide of Example 2.

DETAILED DESCRIPTION

This invention provides a novel nucleic acid/protein construct that characteristically can exist in either of two mutually exclusive states. In general the construct, generally referred to herein as a "flip-flop" comprises a nucleic acid having at least two protein binding sites. The binding sites are situated close to each other so that when a first site is bound by its cognate nucleic acid binding protein the second site cannot be bound (e.g., due to steric hindrances). Conversely, when the second site is bound by its cognate nucleic acid binding protein, the first site cannot be bound. The flip-flop ran thus exist in two possible mutually exclusive states; either the first site bound or the second binding site bound.

It will be appreciated that two state elements such as the flip-flop described herein form the heart of a wide variety of digital information processing and control'systems. In particular, it is explained herein that the flip-flops can act as static or dynamic data storage elements (i.e., each flip-flop acting as a bit, e.g. in a read only memory). In addition, the flip-flops can be assembled into "logic" gates (e.g., AND, OR, NAND, NOR, NOT) that act as computational elements or that can be assembled to control cellular machinery (e.g. the expression of one or more genes). This invent ion thus provides novel methods for regulating gene expression in cells. In addition, the flip-flops of this invention can be used in sequential logic systems (i.e., as true resettable flip-flops) to provide a true molecular binary computational or control system.

1. Flip-Flops, Gates, and Their Uses

A) Simple Data Storage: Read Only Memory (ROM).

The molecular flip-flops of this invention can be used for simple data storage. In effect the molecular flip-flops consisting of a nucleic acid having two mutually exclusive protein binding sites have three discrete states; completely unbound, the first site bound, or the second site bound (see, e.g., FIGS. 1a and 1b). The "flip-flops" could be used to store information encoded in a trinary system.

However, given the general emphasis on binary storage, typically only two states will be used. These will preferably include either bound versus unbound, or site one bound versus site two bound (BS1 vs BS2 in FIGS. 1a and 1b). In the first instance, the unbound state could be designated zero and the bound state one, while in the second case, the first site bound could be designated zero and the second site designated one.

The state of the single nucleic acid molecule (unbound versus bound) or (site one versus site two bound) or a multitude of such nucleic acid molecules can be used to encode and store information.

For example, the origin of products can be tagged at a molecular level. Thus, if a product is from factory A, site one of the flip-flop may be unbound (e.g., state 0), while if a product is from factory B, site one of the flip-flop can be bound (e.g. state 1). A single protein/nucleic acid "flip-flop" thus stores 1 bit of information and, in this example, is able to indicate two different sites of origin. Of course, multiple "flip-flops" can be combined to form "registers" encoding a virtually limitless amount of information.

Figure 2:
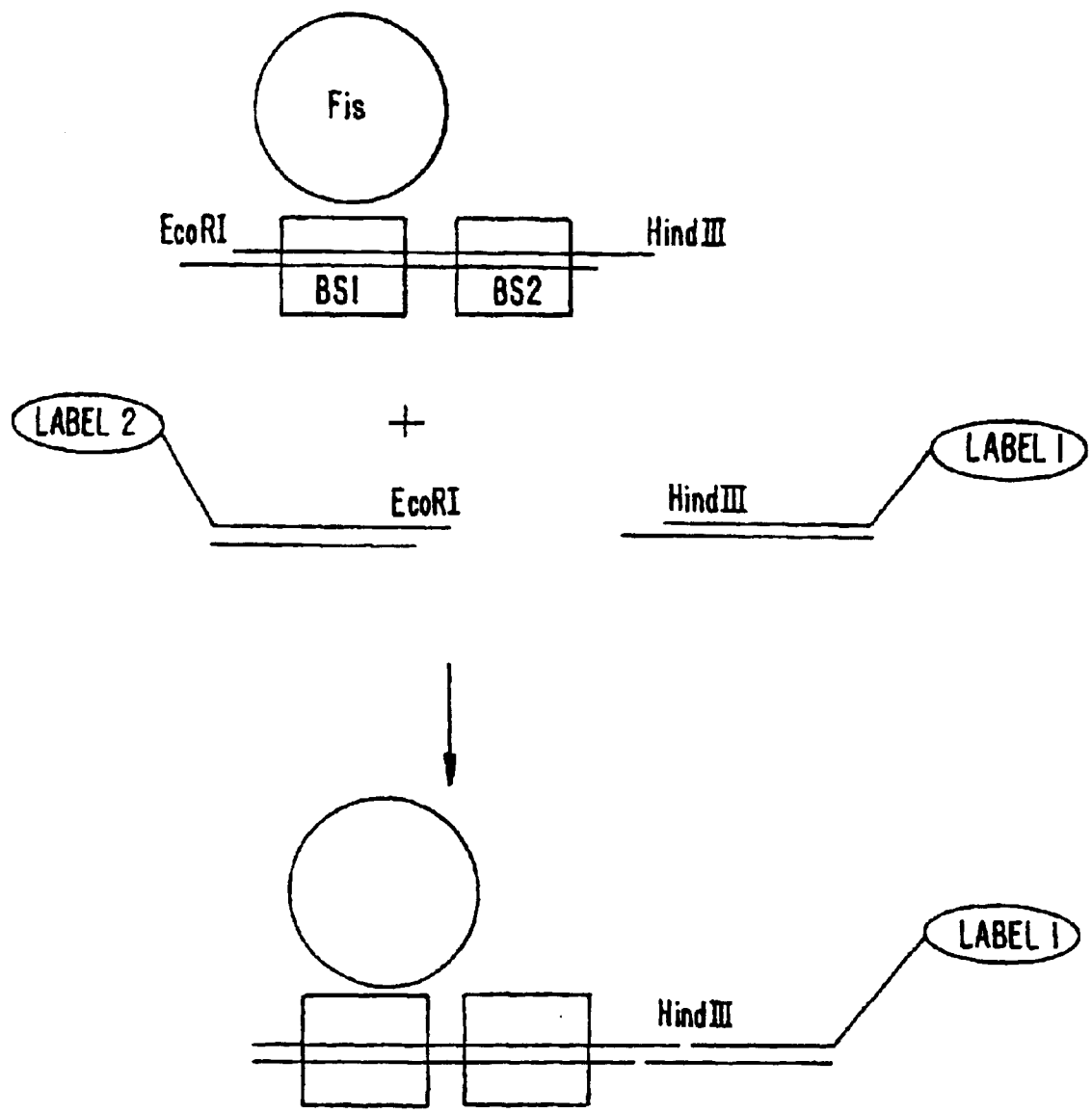
FIG. 2 illustrates readout of a flip-flop using a nucleic acid readout molecule and a ligation reaction. The flip-flop is incubated with two readout molecules one of which has an end complementary to one end of the flip-flop nucleic acid and the other of which has an end complementary to the other end of the flip-flop nucleic acid. The readout molecules, under hybridizing conditions, bind to the respective ends of the flip-flop nucleic acid. A ligase reaction is then run. The bound nucleic acid binding protein (Fis in FIG. 2) blocks access of the ligase to the site adjacent to the bound binding site.(BS1 in FIG. 2) thereby preventing ligation of that readout molecule. The other readout molecule is successfully ligated to the nucleic acid and provides a signal indicating which binding site was not blocked.

Readout can be easily accomplished by any of a number of means. For example, in one embodiment, the flip-flop nucleic acid will terminate with overhangs comprising restriction sites and each end will comprise a different restriction site (e.g., an EcoRI overhang adjacent to binding site 1 and a HindIII overhang adjacent to binding site 2 as illustrated in FIG. 2). The flip-flop is then contacted with two "readout" molecules comprising a double stranded nucleic acid ending in either an EcoRI overhang or a HindIII overhang and a ligation reaction is performed. The ligase will be unable to react at the restriction site adjacent to the blocked (bound) site because of the interference afforded by the binding protein (e.g., Fis). Conversely, the ligase will react at the restriction site adjacent to the blocked (bound) site thereby attaching the "readout" molecule having the matching restriction site. Thus, where binding site one is bound, the readout molecule will attach adjacent to binding site two and where binding site two is bound, the readout molecule will attach adjacent to binding site one.

The readout molecule can be detected by any of a wide variety of means. For example, the two readout molecules can be labeled with distinguishable labels (e.g. fluorescent molecules of different colors). The readout molecules can optionally include a primer site to facilitate PCR amplification of a particular nucleic acid sequence that will only be amplified when the readout molecule is successfully ligated.

The nucleic acid of each the flip-flop can also encode a unique identifier indicating which bit in the register or message is represented by that flip-flop. The PCR reaction can therefore simultaneously reveal both the identity or address of the bit and its state. In another embodiment, the readout sequence can optionally provide a hybridization target for capture of the bit on a solid support (e.g., in a well of a microtiter or PCR plate).

The flip-flop can be provided free in solution or it can be anchored to a solid support (e.g., via a biotin/streptavidin reaction). When anchored, the anchor can be situated so that both ends of the nucleic acid are free (e.g., for the use of two readout molecules) or, it can be anchored through one end.

Where one end of the flip flop is anchored, readout can be accomplished with a single readout molecule having a restriction site complementary to the free end. Successful ligation will indicate that the binding site adjacent to the free end is unbound, while ligation failure will indicate that the binding site adjacent to the free end is occupied (bound).

In another embodiment, the memory can simply consist of a nucleic acid having a single protein binding site and a single protein. In this embodiment, the bound nucleic acid will indicate one state, while the unbound nucleic acid will indicate the other state. This memory can be read by a number of means as described herein. Again, in a preferred embodiment, readout can be accomplished by a ligation reaction. In this case the nucleic acid molecule can comprise a single restriction site adjacent to the protein binding site. The molecule is contacted with a nucleic acid having the complementary restriction site overhang and a ligation reaction is run as illustrated in FIG. 2. When the protein is bound, the ligase cannot react with the restriction site and no ligation reaction occurs. Conversely, when the binding site is unbound, the ligation can occur and the attached readout molecule can then be detected.

Once the state of the flip-flop molecular memory is set, the state can be locked-in by cross-linking the nucleic acid binding protein to the nucleic acid. Many cross-linkers suitable for such immobilization are known and include, but are not limited to agents such as gluteraldehyde, avidin-biotin, and the like. The flip-flop thus provides a "write once read many" (WORM) memory that is extremely stable to variations in environmental conditions.

As suggested above, almost any kind of information can be thus encoded into a series of "flip-flops" and read out at a later time. Such combinations of flip-flops provide messages at the molecular level that can provide useful information (e.g. point of manufacture of controlled substances such as drugs or explosives, unique identifiers or authenticators e.g., currency, documents, etc., and the like).

Where a binding protein having high affinity and stability (e.g., Tus) is used, the message will be relatively stable and if crosslinked, highly stable, to extreme environmental conditions. The message will also be extremely difficult, if not impossible, to detect by casual observation and will require use of the appropriate assay (e.g. ligase reaction with the correct readout molecules) for detection and/or readout.

It will be noted that, in a preferred embodiment, the readout molecule will be designed so that it contains no protein binding site(s) other than those desired. This can be routinely accomplished with the use of "sequence walkers" as described by Schneider (1,997) *Nucleic Acids Res.*, 25: 4408–4415.

B) Molecular Computing

1) Combinatorial Tasks

In digital systems, digital outputs are often generated from digital inputs. For instance, an adder might take two 16 bit numbers as inputs and generate a 16-bit (plus-carry) sum. Alternatively, a system might multiply two numbers another task might be to compare two numbers to see which is larger, or to compare a set of inputs with a desired input to make sure that the systems are equivalent. In another embodiment it might be desirable to attach a "parity bit" to a number to make the total number of 1's even, say before transmission over a data link. Then the parity could be checked on receipt (e.g., subsequent analysis) as a simple check of correct transmission. All of these are tasks in which the output or outputs are predetermined functions of the input or inputs. As a class, they are known as combinatorial tasks. They can all be performed with devices called gates, which perform the operations of Boolean algebra applied to two-state (binary) systems.

The term "gate" as used herein refers to a device that returns an output that is a function of one or more inputs. Both the output and the input are HIGH or LOW signal(s), and in the molecular gates of this invention the signals are carried (indicated) by signal proteins, which are, in a preferred embodiment, nucleic acid binding proteins that bind to particular nucleic acid sequences (binding sites).

In the molecular computers and controls of this invention, the two (binary) signal states are represented by either a protein bound to a nucleic acid at a particular protein binding site (the signal state then being referred to as HIGH in analogy to electronic systems) or a binding site being unbound (referred to herein as LOW in analogy to electronic digital systems).

It will be appreciated that the state of the various gates can be read and thus provide information (e.g., the result of a computational step) or can be used to control a process. In the latter embodiment, the output state need not be read directly, but can simply result in the upregulation (e.g., where the output signal protein is a transcription factor/enhancer) or downregulation (e.g where the output signal protein is a repressor) of one or more genes. The gates can also be stacked so that the output of one gate acts as an input for another gate (e.g one gate activates transcription of a protein binding molecule (signal molecule) that can act as an input for the next gate).

Gates are well known to those of skill in the art. Basic gates include an AND gate, an OR gate, and an Inverter (the NOT function). Other gates include the NOR (NOT OR), the NAND (NOT AND), the exclusive OR (XOR), and so forth. A detailed description of gates can be found for example, in Horowitz and Hill (1990) The Art of electronics, Cambridge University Press, Cambridge.

The construction and use of the NOR gate is described below. It is generally appreciated that the NOR gate can be used to construct all of the other types of gates and thus is sufficient to provide a functional computer. The use of the NOR-gate to construct NOT, OR, AND, and NAND gates is described below. Using the principles outlined herein, other gates can be designed at will.

a) NOR Gate

The output of a NOR gate is HIGH (able to bind a protein) only when both inputs are LOW (unbound). This can be expressed in a "truth table" as shown in Table 1. In the truth tables shown herein, inputs and outputs refer to particular preselected binding sites on an underlying nucleic acid. The inputs are viewed as HIGH when bound by a nucleic acid binding protein (e.g., Fis, LacI, lambda cI, lambda cro, LexA, TrpR, ArgR, AraC, CRP, FNR, OxyR, IHF, GalR, MalT, LRP, SoxR, SoxS, sigma factors, chi, T4 MotA, P1 RepA, p53, NF-kappa-B, ribosomes, T4 regA, spliceosomes (donor and acceptor), polyA binding factor, and the like) also referred to herein as a "signal protein" and as LOW when they are not so bound. The outputs are viewed as HIGH when they are bound or capable of being bound by a nucleic acid binding protein. (A site that is capable of being bound by a polypeptide can be read out as HIGH by providing the signal protein under circumstances where the binding will occur if the site state is HIGH and then detecting the bound protein.) Conversely the outputs are viewed as LOW when they are not or cannot be bound by a nucleic acid binding protein (i.e., the protein that typically recognizes and binds to that biding site). A "1" in the truth tables shown herein represents a HIGH state, while a zero represents a LOW state.

TABLE 1

The truth table of a NOR gate.

| Input 1 $I_1$ | Input 2 $I_2$ | Output $O_1$ |
|---|---|---|
| 0 | 0 | 1 |
| 0 | 1 | 0 |
| 1 | 0 | 0 |
| 1 | 1 | 0 |

As illustrated in Table 1, the NOR gate output is HIGH only when both inputs are low. If there are more than two inputs, the NOR output gate is HIGH only when all of the inputs are low. If any input is set HIGH, the output of the NOR gate is LOW.

Figure 3:
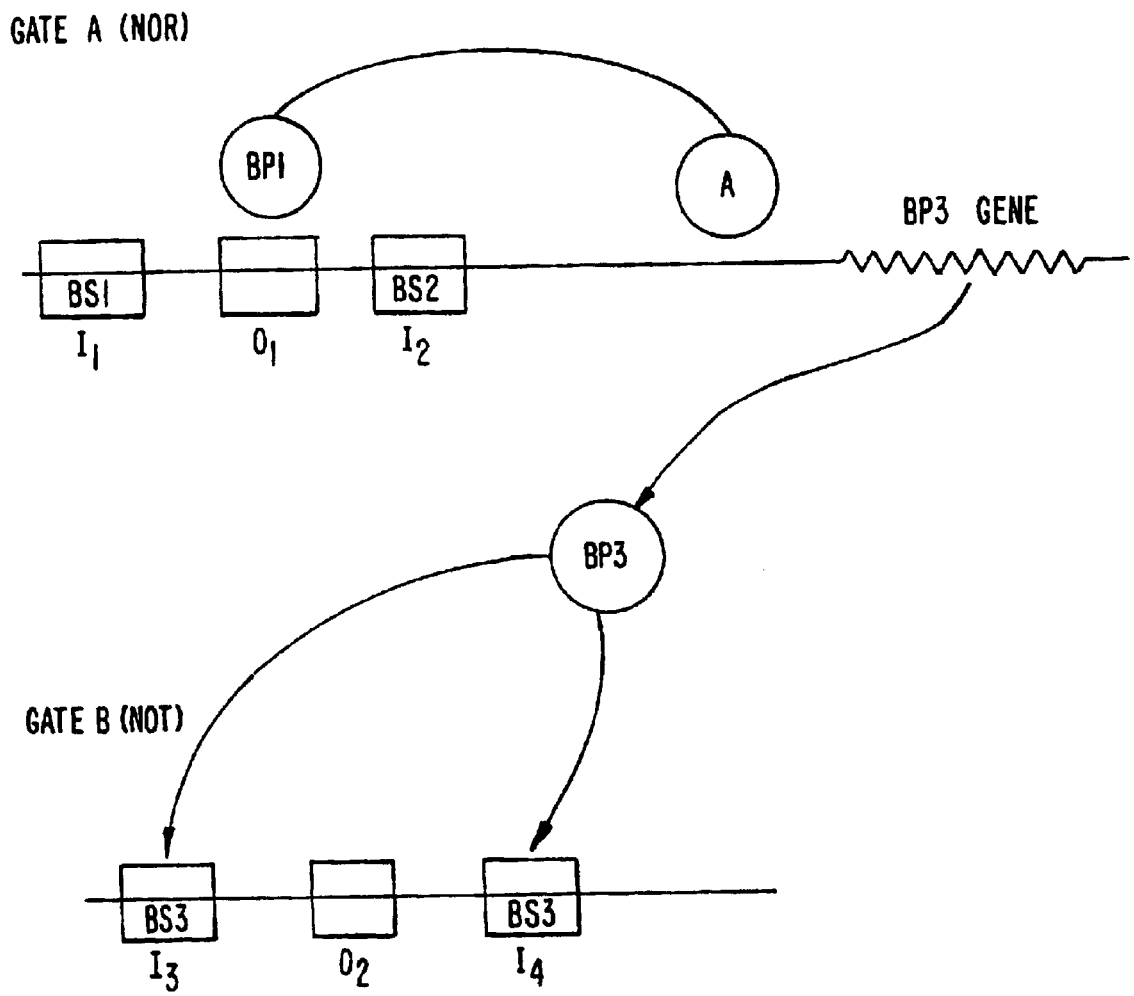
FIG. 3 illustrates a molecular NOR gate, a NOT gate, gene activation under the control of a gate, signal coupling between two gates and a molecular OR gate. Gate A acts as a simple NOR gate, output $O_1$ providing a NOR response to inputs $I_1$ and $I_2$, as described herein. Gate B, in which $I_3$ and $I_4$ are identical provides a molecular NOT gate with $O_2$ providing a NOT response to inputs at $I_3$ or $I_4$ as described herein. Gate A also illustrates regulation of gene expression. When output $O_1$ is HIGH, protein BP1 can bind to that site. This anchors the tethered activator (A) which then activates expression of the gene.

One example of a molecular NOR gate of this invention is illustrated in FIG. 3. A preferred molecular NOR gate comprises a nucleic acid sequence having at least three protein binding sites. Two peripheral "input" binding sites (designated $I_1$ and $_2$ in FIG. 3) bracketing an "output" binding site (designated $O_1$ in FIG. 3). The protein binding sites are spaced so that when either input site ($I_1$ or $I_2$) is bound,-i.e., by a signal protein, the bound protein prevents a nucleic acid binding protein (e.g., a second signal protein) from binding the central "output" ($O_1$) site.

Under these circumstances, the conditions of Table 1 are met. If either input protein binding site is bound with a protein, the output protein binding site cannot be bound. The only condition when the output is HIGH (the output site can be bound) is when both inputs are LOW (unbound).

It will be appreciated that in this, and other gates described herein, the protein binding sites can be selected to bind the same or different proteins. However, where more than one site binds (is recognized by) the same protein, there preferably exists a "selector" mechanism that allows the sites (e.g. the two inputs) to be distinguished by the binding protein. In a preferred embodiment, the selector can be a second molecule (e.g. a DNA binding protein that, when bound blocks the binding of a protein to the respective input or output binding sites). Where the selector molecules differ at each site, the signal molecules can be directed to the particular location simply by use of the appropriate selectors.

In one embodiment, each input specifically binds a different binding protein and the output binds a third different binding protein. Alternatively, the two inputs can bind the same type of binding protein while the output binds a different protein. In this instance only two selectors may be required, e.g. one selector at each input to specify whether $I_1$ or $I_2$ (or $I_3$ . . . if there are more inputs) is bound. The readout binding protein can then be added after the input binding step and no selector is required for the output binding site. From the foregoing explanation, other combinations of the same or different binding proteins and/or selectors will be routinely determined by one of ordinary skill in the art. It will be noted that in one preferred embodiment, the input and/or output DNA binding proteins include, but are not limited to LacI, lambda cI, lambda cro, LexA, TrpR, ArgR, AraC, CRP, FNR, OxyR, IHF, GalR, MalT, LRP, SoxR, SoxS, sigma factors, chi, T4 MotA, P1 RepA, p53, NF-kappa-B, while preferred input and/or output RNA binding proteins include, but are not limited to ribosomes, T4 regA spliceosomes (donor and acceptor), polyA binding factor, and the like.

It will be appreciated that these and other nucleic acid binding proteins can also act as selectors. Alternatively, the selectors can be restriction endonucleases modified so that they bind, but do not cut the bound nucleic acid. The selection and/or design of DNA binding proteins and/or selectors is described below in section II.

b) Coupling the NOR Gate to Another Gate.

As indicated above, in the design of various gates and more elaborate molecular computing circuits it is often desirable to couple the output of one gate to the input of another gate. More particularly, the output of one gate acts as the input to one or more other gates.

For example, the output of a NOR gate can act as the input of a NOR gate to produce an OR gate. In this case, the output ($O_1$) produced by two inputs ($I_1$ and $I_2$) is represented algebraically as:

$$O_1 = OR(I_1, I_2) = NOT(NOR(I_1, I_2))$$

Coupling the output of one gate (or flip-flop) to the input of another gate (or flip-flop) can be accomplished by a number of means. For example, in one embodiment, a single binding site can act as both the output for one gate and the input for another gate. However, in a preferred embodiment, it is generally preferred that the output of one gate or flip-flop and the input of another gate or flip-flop comprise different binding sites. In this instance, the logic elements (gates or flip-flips) can regulate expression of a signaling molecule (binding protein) that acts as an input into one or more logic elements.

A gate regulating expression of a binding protein is illustrated in FIG. 3. While this figure illustrates a NOR gate regulating gene expression this can be accomplished with essentially any gate.

As shown in FIG. 3, readout of the NOR gate is accomplished by contacting the output binding site ($O_1$ in FIG. 3) with a tethered activator. The tethered activator comprises a binding protein capable of specifically binding to the output binding site (e.g., $O_1$) attached (directly or through a linker) to a gene activator (e.g., Gal4, see, e.g., Ptashne (1985) *Cell* 43(3): 729–736). When the output binding site is set HIGH (e.g. by both inputs being set LOW in the NOR gate illustrated in FIG. 3), the binding protein of the tethered activator binds to the output binding site. This anchors the activator which then activates transcription of a gene under the activator's control.

The gene encodes a binding protein (signaling molecule) that, once expressed, can bind to the input binding sites of other logic elements (e.g., gates or flip-flops) thereby setting the input(s) HIGH. Where the output site is set LOW, the tethered activator cannot bind and no transcription occurs. No signaling protein is expressed and the input(s) of "downstream" logic elements stays LOW. Thus, the logic element regulated expression of a signaling molecule (binding protein) couples the output of one logic element with the input of other logic elements.

It is well known that the anchoring of a tethered activator can express gene activation. This was first demonstrated by Ptashne (1985) *Cell* 43(3): 729–736, who showed that GAL4, a *Saccharomyces cerevisiae* transcriptional activator attached to a LexA, an *Escherichia coli* repressor protein could activate transcription of a gene if and only if a lexA operator (a binding site to anchor the construct) was present near the transcription start site. A number of other tethered activator-binding protein constructs have similarly been shown to activate transcription (see. e.g., Silverman et al. (1993) *Proc. Natl. Acad. Sci. USA*, 91: 11665–11668, Chrivia et al. (1993) *Nature*, 365: 855–859, and Pfisterer et al. (1995) *Biol. Chem.*, 270(50): 29870–29880).

The coupling can also be run with the opposite "sign". In this embodiment, the gene that encodes the binding protein can be constitutive active. The output of the logic element can then be bound by a tethered repressor that when bound switches off gene expression. As the binding protein is cleared from the system, the formerly bound (HIGH) input sites will reset to a LOW state. However, in a preferred embodiment, logic element coupling is accomplished with the use of activators to avoid inadvertent and undesired suppression of the signal protein by free repressor in the solution.

c) Inverter (Not) Function.

A second important combinatorial logic function is the inverter or NOT function. The NOT function returns the complement of a logic level. The not function is illustrated by the truth table of Table 2.

TABLE 2

Truth table of the NOT (inverter) function

| Input 1 $I_1$ | Output $O_1$ |
|---|---|
| 0 | 1 |
| 1 | 0 |

A NOT function returns a LOW signal state when the input is HIGH and a HIGH signal state when the input is LOW. In the context of a molecular inverter, binding a protein to an input (thereby setting the input HIGH) prevents binding of a protein to the output binding site thereby setting the output LOW).

Inspection of Table 1 reveals that a NOR gate in which both inputs are equal becomes a NOT gate (inverter function). Thus, where both inputs are set HIGH, the output of a NOR gate is LOW and, conversely, where both inputs are set LOW, the output of the NOR gate is HIGH.

One embodiment of the NOT gate is illustrated by Gate B in FIG. 3. In this gate, both inputs are the same binding site and no selectors are used to control which of the two sites is specifically bound.

When an input binding protein (BP3 in FIG. 3) is present either or both $I_3$ and $I_4$ are bound and set HIGH. The output site ($O_2$) is blocked and thereby set LOW. Conversely, when the input binding protein (BP3) is absent, both $I_3$ and $I_4$ are unbound and therefore set LOW. The output site ($O_2$) is unblocked and can therefore be bound. The output is thus set HIGH. Gate B thus conforms to the truth table illustrated in Table 2.

While the NOT gate is illustrated as an OR gate in which the inputs are set equal, it will be appreciated that one of the inputs can be eliminated with essentially no change in function. For example, if input 3 ($I_3$) is eliminated, a LOW input 4 ($I_4$) will still result in a HIGH output and vice versa. Indeed, both inputs can be eliminated and a single site can be viewed as self-NOT. However, in this instance it becomes difficult to distinguish input from output unless the signal and readout steps are clearly distinguished (e.g., performed at separate times or different input and readout molecules are used).

In a preferred embodiment, the NOT gate is a NOR gate having two input binding sites ($I_1$ and $I_2$) that are identical. The use of two input sites increases the likelihood of detecting an input signal when signaling protein concentration is low.

d) OR Gate

A NOR gate is essentially an inverted OR gate. The converse is also true. Thus, passing the output of a NOR gate through a NOT gate gives OR. Algebraically this may be designated as:

$$O_1 = NOT(NOR(I_1, I_2)) = OR(I_1, I_2)$$

TABLE 3

Truth table of an OR gate.

| Input 1 $I_1$ | Input 2 $I_2$ | Output $O_1$ |
|---|---|---|
| 0 | 0 | 0 |
| 0 | 1 | 1 |
| 1 | 0 | 1 |
| 1 | 1 | 1 |

Generally an OR gate produces a HIGH output (the output protein binding site is available for binding or bound by a signal protein) when any or all inputs are HIGH (binding sites are bound).

A molecular OR gate is illustrated in FIG. 3 which shows a NOR gate feeding an output (BP3) into a NOT gate. The output of the NOT gate ($O_2$) is a NOR of the inputs 11 and 12 into the OR gate (gate A). The NOR gate regulates the expression of a gene as described above. The gene encodes a binding protein (BP3 in FIG. 3) that specifically binds to either of the two inputs (BS3 in FIG. 3) of a NOT gate. When either or both inputs of the first NOR gate (gate A) are set high, the activator is not bound to the output and gene activation does not occur. The input of the NOT gate (Gate B) is set LOW and the output is thereby set HIGH. Conversely, when both inputs of the NOR gate are unbound (LOW), the transactivator (A) can be anchored at $O_1$ resulting in the activation of the gene encoding a binding protein (BP3 in FIG. 3). The binding protein sets the input(s) of the NOT gate high resulting in a LOW output at $O_2$. Thus the only condition in which $O_2$ is LOW is when neither input ($I_1$, or $I_2$) is HIGH. This conforms with the truth table illustrated in Table 3.

As indicated above, one or both of the inputs of the NOT function (Gate B in FIG. 3) can optionally be eliminated. Particularly, where the NOT gate provides input to another gate or function by anchoring a second transactivator, both inputs can be eliminated. Then, when both inputs to Gate A ($I_1$ and $I_2$) are set LOW, the binding protein BP3 will be expressed, bind to the single site ($O_2$) and thereby prevent anchoring of the second transactivator.

e) AND Gate

The output of an AND gate is HIGH (able to bind a protein) only when both inputs are HIGH. An AND gate can be constructed from NOR gates as:

AND($I_1,I_2$)=NOR(NOR($I_1,I_1$), NOR($I_2,I_2$))

This can be expressed in a "truth table" as shown in Table 4. Again, as described above, inputs and outputs refer to particular preselected protein binding sites.

TABLE 4

The truth table of an AND gate constructed of NOR gates.

| Input $I_1$ | Input $I_2$ | X = NOR ($I_1, I_1$) | Y = NOR ($I_2, I_2$) | Output $O_1$ NOR (X, Y) |
|---|---|---|---|---|
| 0 | 0 | 1 | 1 | 0 |
| 0 | 1 | 1 | 0 | 0 |
| 1 | 0 | 0 | 1 | 0 |
| 1 | 1 | 0 | 0 | 1 |

Figure 4:
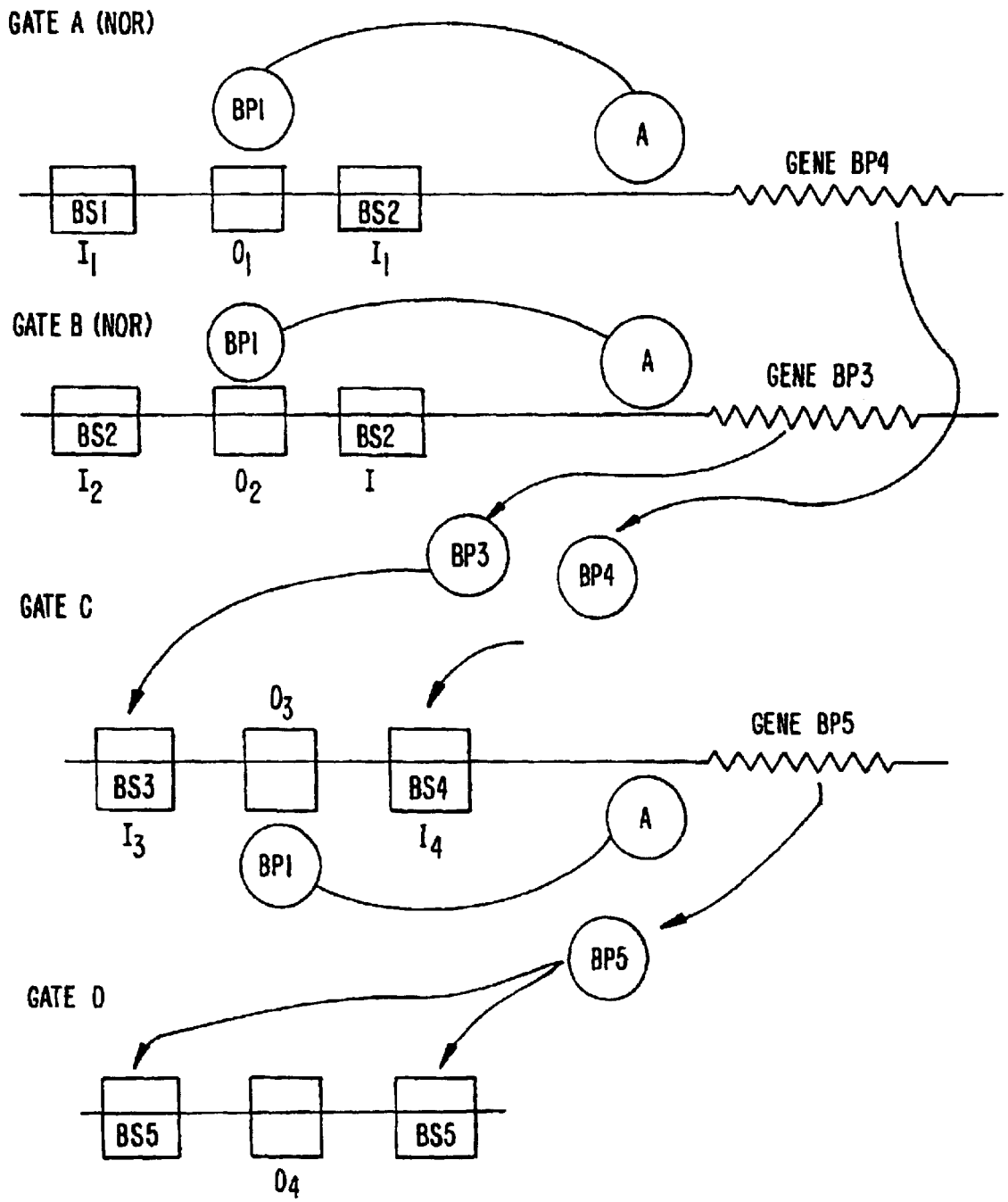
FIG. 4 illustrates an AND and a NAND gate. Two NOR gates, gates A and B. provide inputs into a third NOR gate (gate C). This produces an output at $O_3$ that is an AND function of the inputs to gates A and B ($I_1$ and $I_2$). Inversion of the AND signal by NOT gate D results in a NAND at output $O_4$ in response to inputs at $I_1$ and $I_2$. The input sites of gates A, B, and D are identical so these NOR gates act as simple inverters.

One AND gate of this invention is illustrated in FIG. 4. The AND gate consists of three NOR gates (described above). The first two NOR gates (Gates A and B in FIG. 4) accept inputs $I_1$ and $I_2$ respectively. It will be noted that two input binding sites in each NOR gate are the same so that in effect the NOR gates act as NOT functions. When the inputs of the NOR gates are set LOW, a binding protein (BP1 in FIG. 4) binds to the output binding site(s) ($O_1$ and/or $O_2$) thereby anchoring a transactivator that activates transcription of binding proteins from each of the OR gates (BP2 and/or BP3 in FIG. 4). The binding proteins then act as inputs into the third gate (gate C). The only condition under which the output ($O_3$) of the third NOR gate is high is when both $I_1$ and $I_2$ of gate A are HIGH resulting in no transcription of BP4 or BP3. This satisfies the conditions of Table 4.

Figure 5A:
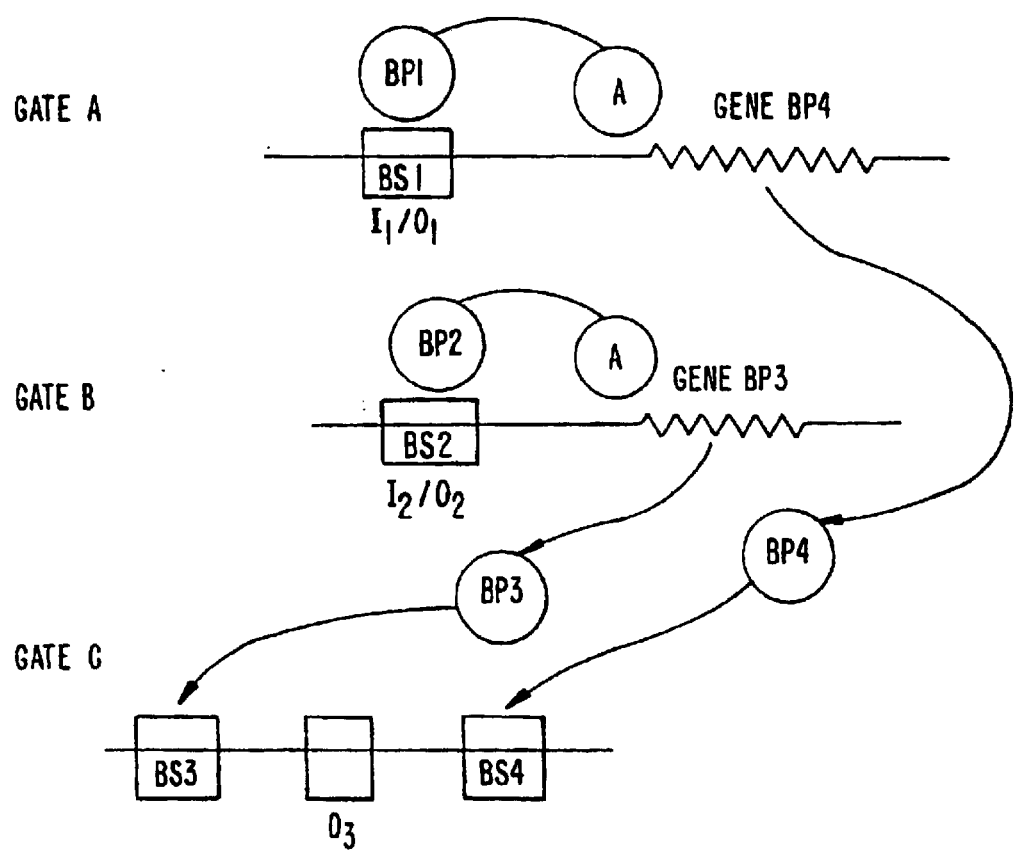
FIG. 5a illustrates a simplified AND gate in which the same binding site acts as both an input and an output for gates A and B.

While the AND gate is illustrated as a series of NOR gates in FIG. 4, since both gates A and B are actually NOT functions, in some embodiments, one or both inputs can be eliminated. Thus, the AND gate can be reduced to a collection of five binding sites as illustrated in FIG. 5a. However, in this instance, it is preferable to use different binding sites for the inputs so as to distinguish them.

Figure 5B:
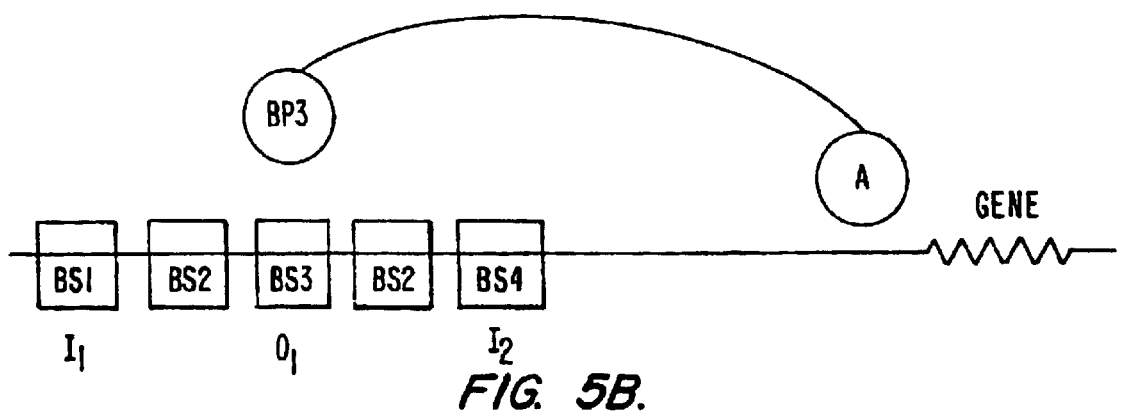
FIG. 5b illustrates a second simplified AND gate utilizing five protein binding sites. The AND gate is illustrated with a tethered binding protein activating a gene.

Another simplified AND gate is illustrated in FIG. 5b. This AND gate consists of five protein binding sites as well. Each pair of adjacent binding sites is capable of acting as a flip-flop (i.e. the constituent sites in a pair are mutually exclusive). When either, or both, $I_1$ and $I_2$ is unbound (LOW) a binding protein can bind to site(s) BS2. When either BS2 site is bound, site BS3 is blocked and $O_1$ is thus set LOW. The only-condition under which BS3 can be set high is when both $I_1$ and $I_2$ are bound. Then no protein binds at BS2, and BS3 ($O_1$) is unblocked (HIGH).

f) NAND Gate

The output of a NAND (NOT AND) is shown in Table 5. The NAND gate is essentially an inverted AND gate. This gate produces a LOW output only when both inputs are set HIGH.

TABLE 5

The truth table of a NAND gate.

| Input 1 $I_1$ | Input 2 $I_2$ | Output $O_1$ |
|---|---|---|
| 0 | 0 | 1 |
| 0 | 1 | 1 |
| 1 | 0 | 1 |
| 1 | 1 | 0 |

A molecular NAND gate of this invention is illustrated in FIG. 4. As explained above, gates A, B, and C form an AND gate. The output of this AND gate (BP5) is run through a NOT gate (gate D) which inverts the signal producing a NAND gate at output $O_4$ in response to inputs $I_1$ and $I_2$.

g) Other Gates.

Using the principles described above, virtually any type of gate can be constructed from the proper combination of NOR and NOT. The identities of various gates are well known to those of skill in the art and can also be determined from first principles of boolean algebra. Various gates are illustrated in Horowitz and Hill, supra. as well as in numerous other references pertaining to digital circuitry.

While the NOR and NOT gates comprising the various constructs in FIGS. 3, 4, and 5 are illustrated as separate nucleic acids, it will be appreciated that the various elements, gates, and even complex digital circuits can exist on and be encoded by a single nucleic acid.

It is also noted that the same species of tethered transactivator (i.e., same binding protein, activator protein combinations) can couple numerous different gates. By placing this activator under logic control, entire circuits can be controlled by a single input.

2) Sequential Logic: The basic flip-flop.

In combinatorial circuits, the output is determined completely by the existing state of the inputs. There is no "memory", no history in these systems. In contrast, in sequential logic systems the output is not determined entirely by the input, but is also affected by the history of the system.

When devices with "memory" are added to the system, it becomes possible to construct counters, accumulators, and other functions that have a historical element.

The basic unit of storage is the "flip-flop". Generally speaking a flip-flop is a device (or system) that has two stable states; it is said to be "bistable". Which state the flip-flop is in depends on its past history.

a) The Basic Flip-Flops and Storage Registers.

A basic flip-flop of this invention is illustrated in FIGS. 1a and 1b. A nucleic acid is provided having two protein binding sites positioned such that they cannot simultaneously be occupied by a nucleic acid binding protein. Thus, if a first site (e.g., BS1 in FIG. 1a) is bound (HIGH), the second site (BS2 in FIG. 1a) is unbound (LOW), conversely, if the second site is bound (HIGH), the first site is unbound (LOW). The flip-flop thus has two stable states: the first site HIGH and the second site LOW or the second site HIGH and the first site LOW.

Binding of the signal polypeptide (BP1 or BP2 in FIGS. 1a and 1b) can be reversible or irreversible. Where the binding is irreversible, the flip-flop acts as a read only storage device (read only memory ROM) and each flip-flop stores one bit of information. As explained above, the flip-flops can be combined (e.g., to form storage registers) and can ultimately encode vast amounts of information. Such registers include at least two and may include even more flip-flops (e.g., up to 3, 4, 5, 6, . . . 4096 or even more flip-flops).

One particularly preferred flip-flop comprises a deoxyribonucleic acid (DNA) having two Fis binding sites. The sites are spaced apart by less than 23 base pairs (bp), preferably less than about 20 bp, most preferably less than about 15 bp and most preferably less than about 12 bp. In one most preferred embodiment, the Fis binding sites are 7 or 11 base pairs apart (see e.g., Example 1) but it will be appreciated that the sites can fully overlap and can be separated by a spacing of 1–11 base pairs. As illustrated in FIG. 8, spacing (expressed in base pairs) refers to the shift in base pairs from fully overlapping sites. Thus a spacing of 0 means the two sites fully overlap. A spacing of 7 bp means that the binding sites are displaced relative to each other by 7 base pairs. In the case of the Fis binding sites of FIG. 8, where the binding site is 21 bp in length, when the sites are spaced apart by 7 bp, there still exists a 14 bp overlap (see, e.g. FIG. 8).

In a preferred embodiment, the Fis binding sites are selected to provide a binding strength of at least about 0 bits, preferably at least about 1 bit, more preferably at, least about 2 bits and most preferably at least about 2.4 bits as determined by individual information theory (see, Hengen et al. (1997) supra.). In one preferred embodiment, one or more of the binding sites in a molecular flip-flop or gate of this invention is a Fis binding site having the sequence (TTTG (G/C)TCAAAATTTG A(G/C)CAAA, SEQ ID NO: 1). The binding sites are preferably spaced from 7 to about 11 base pairs apart and more preferably are spaced at 7 or 11 base pairs apart (see. e.g., Example 1). Particularly-preferred paired-binding sites include, but are not limited to, 11 bp spacing (e.g., 5'-TATTCTTTGCTCAAAATTTGATC-AAATTTTGAGCAAAGAATA-3', SEQ ID No: 2) and 7 bp spacing (e.g., 5'-AGGCTTTTGCTCAAAGTTTAAAC-TTTGAGCAAAAGCCT-3', SEQ ID NO: 3) whose walker maps are illustrated in FIG. 8. Particularly preferred Fis-based flip-flops are illustrated in the Examples.

b) Setting the State of the Flip-Flop.

The state of the flip-flop is set by binding a protein to either the first or to the second binding site (BS1 or BS2 in FIGS. 1a and 1b). The state can be set randomly or alternatively, the flip-flop can be set to a particular preselected state (i.e., it is predetermined whether the first or second binding site will be occupied). Where the two binding sites bind to characteristically different nucleic acid binding proteins (e.g. Fis binds at the first site and CRP binds at the second site), the state of the flip-flop can be set by providing one of the two binding proteins. Alternatively, the flip-flop can be used to read the relative abundance of the two proteins. To the extent one binding protein is present in greater concentration than the other, the predominance of flip-flops in one state as opposed to the other will indicate the relative abundance of the proteins. The flip-flop may be used alone to achieve such a readout or may be used in conjunction with one or more other flip-flops and/or gates to provide such a readout as described below.

Alternatively, both binding sites of the flip-flop may bind to the same binding protein (e.g. Fis). In this case, setting the flip-flop to a particular predetermined state may require the use of a selector.

A selector is a moiety that prevents binding of the binding protein to a particular binding site. Thus, for example in FIG. 1b, if a selector is bound to selector binding site $S_1$, then binding site BS1 cannot be occupied and the flip-flop is set with site BS2 HIGH. Conversely if the selector $S_1$ in FIG. 1b is occupied the binding protein can only bind to site BS1 and BS1 is then set HIGH.

Selectors are discussed below. However, at this point it is noted that the selector can be a binding protein or any other moiety that selectively blocks the binding site with which it is associated. Thus, the selector can be a modified restriction endonuclease (e.g., EcoRI) that binds to, but does not cleave the underlying nucleic acid (see, e.g., see, King et al. (1989) *J. Biol. Chem.* 264(20): 11807–11815). The selector could also be a chemical that selectively modifies the underlying nucleic acid (e.g., base modification, thymidine dimerization, etc.) to prevent attachment of the binding protein. Other possible selectors include nucleic acids (e.g., antisense molecules) peptide nucleic acids, streptavidin/biotin, and the like.

c) Resetting the State of the Flip-Flop.

As indicated above, the flip-flop can use proteins that bind nucleic acids irreversibly and thus act as a read-only memory component. Alternatively, binding proteins can be used that can be released from the flip-flop. Thus the state of the flip-flop can be set by binding a binding protein to one site and then reset by releasing that protein (and preferably binding a protein to the other site).

Nucleic acid binding proteins that bind reversibly are known to those of skill in the art and include, but are not limited to LacI, lambda cI, lambda cro, LexA, TrpR, ArgR, AraC, CRP, FNR, OxyR, IDF, GalR, MalT, LRP, SoxR SoxS, sigma factors, chi, T4 MotA, P1 RepA, p53, NF-kappa-B, ribosomes, T4 regA, spliceosomes (donor and acceptor), polyA binding factor, and the like.

In addition, non-naturally occurring binding proteins can be obtained by the mutation and selection of natural binding proteins or by de novo synthesis. The identification and preparation of suitable nucleic acid binding proteins is described below in Section II.

3) Combinations of Gates to Form Logic Circuits.

It will be appreciated that logic gates and flip-flops of this invention can be combined in a wide variety of ways to process signals. This involves coupling the output of one gate to an input of another gate. This is illustrated above, where the output of the NOR gate is coupled to (provides) the input of the inverter to produce an OR gate. Similarly, the output of the AND gate is coupled to an inverter to produce a NAND gate. Of course more than two gates may be coupled into a circuit and the coupling may be to gates other than an inverter. Indeed virtually any type of gate can be coupled to any other type of gate.

Using the gates illustrated herein, numerous other logic functions will be apparent to those of skill in the art.

Moreover, extending the principles of gate formation and coupling described above, various combinations of gates and/or flip-flops can be combined to produce complex computational signal and/or control circuits. One example of such a circuit is the use of gates to produce a simple adder. The adder Circuit is well known and described, for example, by Gonick (983) The Cartoon Guide to Computer Science, Barnes & Noble Books, New York, N.Y.

Briefly, components of a one bit adder can be made from XOR and AND gates and a carry bit. When the carry is 0, the SUM is the XOR of the addends, while the CARRY is the AND of the addends. Thus, where c is a previous carry, a is one addend and b is the other addend the adder meets the conditions of Table 6.

TABLE 6

Adder logic in which carry bit is 0.

| c | a | b | Sum a XOR b | Carry a AND b | Value |
|---|---|---|---|---|---|
| 0 | 0 | 0 | 0 | 0 | 0 + 0 = 0 |
| 0 | 0 | 1 | 1 | 0 | 0 + 1 = 1 |
| 0 | 1 | 0 | 1 | 0 | 1 + 0 = 0 |
| 0 | 1 | 1 | 0 | 1 | 1 + 1 = 10 (i.e., "2") |

As evidenced by Table 6, this is indeed the sum and carry. When the input carry is 1, the table changes a little as shown in Table 7.

TABLE 7

Adder logic in which carry bit is 1.

| c | a | b | Sum NOT (a XOR b) | Carry a OR b | Value |
|---|---|---|---|---|---|
| 1 | 0 | 0 | 1 | 0 | 1 + 0 + 0 = 1 |
| 1 | 0 | 1 | 0 | 1 | 1 + 0 + 1 = 10 ("2") |
| 1 | 1 | 0 | 0 | 1 | 1 + 1 + 0 = 10 ("2") |
| 1 | 1 | 1 | 1 | 1 | 1 + 1 + 1 = 11 ("3") |

If there is a carry from the previous one bit adder, the sum is NOT(XOR(a,b)) and the CARRY is OR(a,b). The input carry c can be used to select these states and make equations:

SUM=(NOT(c) AND XOR(a,b))

(c AND NOT(XOR(a,b)))

or

CARRY=(NOT(c) AND AND(a,b))

or (c AND OR(a,b))

As indicated above other logic functions can be produced using similar approaches. Signal processing and control circuits comprising a multiplicity of coupled gates are well known to those of skill in the art (see, Horowitz and Hill, supra.).

While the NOR and NOT gates comprising the various constructs in FIGS. 3, 4, and 5 are illustrated as separate nucleic acids, it will be appreciated that the various elements, gates, and even complex digital circuits can exist on and be encoded by a single nucleic acid. The combination of flip-flops and NOR gates with activators leading to transcription of the next logic level means that individual yeast (or other) cells could be used to perform molecular logic.

It will also be appreciated that these circuits are essentially equivalent to their digital electronic counterpart. These circuits, however exist on the molecular level. Moreover, they can be produced in enormous numbers (e.g. through simple expression from appropriate vectors) and thus are amenable to enormous parallelism and are therefore well adapted to the solution of certain classes of complex computational problems.

It is noted, for example, that nucleic acid constructs have been used to solve a directed Hamiltonian path problem (Adleman (1994) *Science*, 266: 1021–1024). Moreover, following Schneider (1991 ) *J. Theoret. Biol.*, 148: 125, Adleman concluded that molecular computation approaches theoretical efficiencies as much as 10 orders of magnitude greater than conventional supercomputers.

4) Signal Readout.

A wide variety of means can be used to read the status of one or more gate outputs or flip-flops. As indicated above, a gate output is read as HIGH where it is bound or capable of being bound by a signal protein. Thus, in a preferred embodiment, the output status can be determined simply assuring that the output site is contacted with an appropriate signal protein under conditions in which, if the site is HIGH and unbound, the signal protein can bind, and then determining the presence or absence of a bound signal protein.

Methods of identifying the binding of proteins to nucleic acids are well known to those of skill in the art. In one embodiment, this can be accomplished by gel shift assays as described herein in the Examples (see, also, Lane et al. (1992) *Microbiol. Rev.* 56(4): 509–528 and Garner et al. (1981) *Nucl. Acids Res.*, 9(13): 3047–3060).

However, the binding can be more easily assayed by detecting the binding of a labeled signal molecule. Means of labeling proteins are well known to those of skill (see, for example, Chapter 4 in *Monoclonal Antibodies: Principles and Applications*, Birch and Lennox, eds. John Wiley & Sons, Inc. N.Y. (1995) which describes conjugation of antibodies to labels and other moieties). Proteins contain a variety of functional groups; e.g., carboxylic acid (COOH) or free amine (—$NH_2$) groups, which are available for reaction with a suitable functional group on either the label or on a linker attached to the label.

Detectable labels suitable for use in the present invention include any composition detectable by spectroscopic, photochemical, biochemical, immunochemical, electrical, optical, genetic or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oregon, USA), radiolabels (e.g., $^3H$ $^{125}I$, $^{35}S$, $^{14}C$, or $^{32}P$), enzymes (e.g., horse radish peroxidase, alkaline phosphatase and others commonly used in an ELISA), selectable markers (e.g., antibiotic resistance genes), and colorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

In another embodiment, the binding of a protein to a particular site on a nucleic acid can be determined by changes in fluorescence of a fluorophore attached either to the binding protein or to the nucleic acid caused by energy transfer between the fluorophore and a quencher molecule or a second fluorophore (e.g., a fluorescence resonance energy transfer system) on protein binding. Thus, for example, a lumazine derivative has been used in conjunction with a bathophenanthroline-ruthenium complex as an energy:transfer system in which the lumazine derivative acted as an energy donor and the ruthenium complex acted as an energy receptor. The lumazine derivative and ruthenium complex were attached to different nucleic acids. Energy transfer occurred when the two compounds, were brought into proximity resulting in fluorescence. The system provided a mechanism for studying the interaction of molecules bearing the two groups (see, e.g., Bannwarth et al. (1991), *Helvetica Chimica Acta*. 74: 1991–1999, Bannwarth et al. (I 991), *Helvetica Chimica Acia*. 74: 2000–2007, and Bannwarth et al., European Patent Application No. 0439036A2).

Such resonance energy transfer systems are easily adapted to detect protein nucleic acid interactions as well. This involves placing the fluorophore or quencher near the particular binding site it is desired to "read" and then detecting the change in fluorescence as the respectively labeled protein binds to that site. Alternatively, the binding protein can carry the flurophore while the DNA carries the quencher or vice versa, and the intensity of fluorescence will then indicate the state of the flip-flop. Other energy transfer systems are well known to those of skill in the art (see, e.g., Tyagi et al. (1996) *Nature Biotechnology*, 14: 303–308). Such systems can readily distinguish between the two stable states of a flip-flop as well simply by providing different quenchers or different fluorophores at each binding site.

As suggested above, the state of a flip-flop or gate can be locked prior to reading by covalently attaching the nucleic acid binding protein (if present) to the underlying nucleic. This can be accomplished by the use of cross-linkers. Protein and nucleic acid cross-linkers are well known to those of skill in the art and include, but are not limited to gluteraldehyde, disuccinimidyl suberate (DSS) (Pierce, Rockford, Ill., USA), active esters of N-ethylmaleimide (see, e.g., Lerner et al. (1981) *Proc. Nat. Acad. Sci. USA*. 78: 3403–3407 and Kitagawa et al. (1976) *J. Biochem.*, 79: 233–236), and the like.

In another embodiment the state of the flip-flop and/or gate can be read by the use of a surrogate marker (a readout molecule) that can optionally preserve the state information even after the binding protein(s) is removed from the underlying nucleic acid. One example of the use of such a readout molecule is described above in the use of ligation reactions to attach a readout nucleic acid to one or the other end of a flip-flop.

Another surrogate readout molecule utilizes an avidin (streptavidin)/biotin interaction. In this embodiment, a biotin is attached to the underlying nucleic acid (preferably via a linker). The biotin is located nearby one of the flip-flop binding sites or near the output site of a gate. After the state of the gate or flip-flop is set, the logic element is contacted with an avidin or streptavidin molecule. When the binding site is occupied by a nucleic acid binding protein (HIGH), the binding protein will block the interaction of the streptavidin with the biotin. Conversely, when the binding site is unbound (LOW), the streptavidin can bind the biotin. The bound streptavidin can be detected using standard methods (e.g. gel shift assay or labeled streptavidin) and a bound streptavidin will indicate a LOW binding site state. The biotin/streptavidin interaction is extremely stable and the state can be read even after the nucleic acid binding protein is dissociated from the underlying nucleic acid. An illustration of this readout system is provided in Example 2.

C) Complex ("digital") Control of Gene Expression

In another embodiment, the signal protein need not be labeled at all in order to detect the state of the output site. For example, where a tethered activator is used to bind to the output site (e.g., as shown in FIG. 3), binding of the tethered activator will induce activation of the appropriately located gene. Where the input signal serves to block an output site (e.g. in the NOR gate), the tethered activator will fail to bind and gene transcription will not occur. Detection of the expression of a gene or genes under the control of these tethered activators (or repressors) then provides an indication of the status of the output. Thus, for example, where the tethered activator is a transcription activator, upregulation of gene transcription indicates a HIGH state at the output. Conversely, where the tethered construct protein is a repressor, and the gene is constitutively activated, a decrease in transcription indicates a HIGH output state.

In this case, where it is desired simply to "read" the output state, the gene or genes under the control of the gate will typically be reporter gene(s). A reporter gene is a gene that that codes for a protein whose activity is easily detected, allowing cells expressing such a marker to be readily identified. Such markers are well known to those of skill in the art and include, but are not limited to glucuronidase, bacterial chloramphenicol acetyl transferase (CAT), beta-galactosidase (β-gal), various bacterial luciferase genes encoded by *Vibrio harveyi, Vibrio fischeri*, and *Xenorhabdus luminescens*, the firefly luciferase gene FFlux, green fluorescent protein, and the like.

Selectable markers (e.g., antibiotic resistance genes) provide another simple mechanism for reading out the state of a flip-flop. In this embodiment, the gene or one of the genes under control of a logic element of this invention is a selectable marker. Cells containing the logic cassette are grown under selection conditions (e.g., in the presence of one or more antibiotics) and survival of the cells indicates the state of the logic element.

In another embodiment the logic gates of this invention can be used for expression control rather than computation. In this case, the reporter gene can be substituted with one or more genes whose expression it is desired to regulate using the logic apparatus of this invention. Such genes include, but are not limited to the multidrug resistance gene (MDRI), e.g., to confer drug resistance on healthy cells during chemotherapy, the p53 tumor suppressor gene, e.g., in certain breast cancers, the telomerase gene, and the like.

This invention thus provides means of regulating gene expression in response to complex stimuli. A simple example, is illustrated in FIG. 3 which shows a gene under the control of a NOR gate. The output of the NOR gate is "read" by a tethered activator having, at one end, a binding protein that specifically recognizes the output binding site and at the other end a gene activator (A). In this case when either input 1 ($I_1$) or input 2 ($I_2$) is bound, the tethered construct cannot anchor to the output site ($O_1$) and the activator attached to the tethered construct fails to activate the gene. However, when both inputs are unbound, the tethered construct attaches to the output site ($O_1$) anchoring the activator to the nucleic acid where it can then activate transcription of the gene.

The source of the two input (signal) proteins can be exogenous (preferably delivered to the cell by a transporter, e.g. lipsome or other vehicle) or heterologous. Alternatively, one or more of the signal protein can be the product of endogenous metabolic pathways in the cell or they can either or both be the product of heterologous expression cassettes which themselves can be simple traditional cassettes (inducible or constitutive) or can be "logic" cassettes having genes under the expression of one or more logic gates and/or flip-flops of this invention. Similarly, the tethered activator (s) can be exogenously supplied, or alternatively, particularly where the linker joining the binding protein and the activator is itself a polypeptide (thereby providing a tethered activator that is a fusion protein), the tethered activator can be expressed as a heterologous polypeptide by an appropriate expression cassette.

In one embodiment, the regulated gene can itself be a nucleic acid encoding a binding protein or multiple genes can be expressed by the "logic cassette" one or more of which is another signaling protein (nucleic acid binding protein) as described above. The expressed nucleic acid binding proteins can act as inputs to the logic cassette providing negative or positive regulation of gene expression by that cassette. Alternatively, or in combination with such feedback regulation, the expressed binding proteins can act as inputs into other logic cassettes thereby allowing cascade regulation of multiple logic cassettes and extremely complex regulation of the gene or genes expressed by the logic cassettes.

The logic-based expression control systems of this invention thus provide a vast improvement in regulation of the expression of heterologous genes (or cDNAs). In traditional heterologous gene expression systems, gene expression is typically regulated by a single inducer (e.g., IPTG). In contrast, expression of a gene (or cDNA) under the control of one or more logic elements as described above can be the result of a complex combination of stimuli including one or more inducers, positive and negative feedback regulation, and the like.

D) Affinity Chromatography/Analyte Quantification.

In a somewhat more mundane, but highly useful application, the flip-flops of this invention can be used to efficiently quantify the amount of an analyte in a solution (e.g., in a biological sample such a cell homogenate, blood, etc.). In this embodiment, both binding domains of the flip-flop are identical and selected to specifically bind to the analyte of interest (e.g., a nucleic acid binding protein (e.g., Fis) or a nucleic acid, etc.). The sites are still positioned however so that binding of the target analyte at one site excludes binding at another site.

The provision of two binding sites on each nucleic acid molecule enhances the probability of binding, as compared to a system in which each nucleic acid bore a single binding site. Because the number of binding sites is doubled the likelihood of the target analyte finding and correctly orienting to an appropriate binding site is increased. However once bound, the second binding site becomes unavailable. Thus, the number of bound nucleic acids is equivalent to the number of bound target analytes. Quantification of the bound nucleic acid thus provides a direct measure of the quantity of bound target analyte and an indirect measure of the amount of analyte in the solution.

The amount of bound nucleic acid can be quantified by a number of means well known to those of skill in the art. For example, an electrophoretic gel can be used to separate the bound from the unbound nucleic acid and unbound analyte. The separated bound nucleic acid can then be quantified e.g., an electrophoretic gel can be used to separate the bound from the unbound nucleic acid and unbound analyte. The separated bound nucleic acid can then be quantified e.g., by quantification of a label that is attached to the nucleic acid. The nucleic acid can be labeled by a number of means as described above.

Such assays are performed in a manner analogous to immunoassays, which also just detect and/or quantify binding of an antibody to a target analyte. Formats for such binding assays are well known to those of skill in the art and include, but are not limited to competitive assay formats, non-competitive assays formats, and other formats (see, e.g., U.S. Pat. Nos. 4,366,241; 4,376,110; 4,517,288; and 4,837,168). For a review of the general immunoassays and binding assay formats, see also Methods in Cell Biology Volume 37: Antibodies in Cell Biology, Asai, ed. Academic Press, Inc. New York (1993); Basic and Clinical Immunology 7th Edition, Stites & Terr, eds. (1999).

II. Assemble of Molecular Flip-Flops and Gates

A) Binding Protein/Nucleic Acid Design/Selection

1) Identification and selection of binding sites.

Many nucleic acid binding proteins and their cognate binding sites are suitable for the practice of this invention. Generally, a suitable protein will bind to a "substrate" nucleic acid (e.g., single or double stranded, RNA, DNA, peptide nucleic acid, etc.) at a site characterized by a particular nucleotide sequence. This site, designated a protein binding site, can vary in sequence and it will be appreciated that for any particular binding protein there may exist a number of different nucleotide binding sites that, while still specific for the binding protein, bind that protein with different strengths (see, e.g., Hengen et al. (1997) supra.).

The binding protein/binding site combinations to be used will be determined by consideration of a number of different factors. These include the number of different binding proteins it is desired to use in the particular system, whether binding at a particular site is to be reversible or irreversible, and what binding site spacing is desirable.

A large number of suitable binding protein are known to those of skill in the art. These include, but are not limited to Fis, LacI, lambda cI, lambda cro, LexA, TrpR, ArgR, AraC, CRP, FNR, OxyR, IHF, GalR, MalT, LRP, SoxR, SoxS, sigma factors, chi, T4 MotA, P1 RepA, p53, NF-kappa-B, ribosomes, T4 regA spliceosomes (donor and acceptor), polyA binding factor, and the like.

Particularly preferred binding proteins are those that when their binding sites are spaced suitably close together, block binding of the cognate protein of the "adjacent" site. Such proteins can be identified by simple screening. This entails providing a nucleic acid (e.g. a double stranded DNA) containing the binding sites at various spacings and then, determining at what spacing the two proteins bind exclusively. An illustration of such an assay is provided in the Examples.

Appropriate binding site spacings (e.g., overlapping sites) can be engineered using individual information theory (see, e.g., U.S. Ser. No. 08/494,115, filed on Jun. 23, 1995, Hengen et a. (1997) supra., Schneider (1991) *J. theoret. Biol.*, 148: 125, and Schneider (1997) *Nucl. Acids Res.*, 25: 4408–4415). In one approach, sequence walkers for all the required components are displayed for a sequence. The sequence is then modified while the quantitative effect on each walker is observed (see, e.g., Example 1 and FIG. 8). For example, it is possible to engineer restriction enzyme site into a Fis site while maintaining the same strength of the Fis site (see, e.g., Schneider (1997) *Nucl. Acids Res.*, 25: 4408–4415). Thus design of the overlapping sites for the logic components is straightforward and can be accomplished computationally.

Nucleic acid binding proteins whose binding sites appear to be closely associated (e.g. in pairs) in nature are expected to provide particularly good candidates for naturally occurring blocking sites. Searches for the occurrence of such binding sites can be accomplished computationally using deposited (e.g., GenBank) sequence information. Methods of searching for and identifying such binding sites using "Sequence Walkers" are described in Schneider (1997) *Nucl. Acids Res.*, 25: 4408–4415, and in copending application U.S. Ser. No. 08/494,115, filed on Jun. 23, 1995.

It is expected that for most protein binding sites, the exclusionary spacing will range from about 0 base pairs (complete overlap), to about 60 base pairs, preferably from about 0 base pairs to about 40 base pairs, more preferably from about 0 or 1 base pair to about 20 base pairs and most preferably from about 7 to about 11 base pairs.

Where the flip-flop state or the inputs or outputs is to be altered (reset) it is desirable to use nucleic acid binding proteins that bind reversibly to the nucleic acid. Such reversible binding proteins are known to those of skill in the art and include, for example, Fis, LacI, lambda cI, lambda cro, LexA, TrpR, ArgR, AraC, CRP, FNR, OxyR, IHF, GalR, MalT, LRP, SoxR, SoxS, sigma factors, chi, T4 MotA, P1 RepA, p53, NF-kappa-B, while preferred input and/or output RNA binding proteins include, but are not limited to ribosomes, T4 regA, spliceosomes (donor and acceptor), polyA binding factor, and the like.

2) GTPase-like Binding Proteins.

One particular preferred group of reversibly binding proteins are those for which release can be accomplished with the consumption of an energy source (e.g. hydrolysis of ATP or GTP to ADP or GDP respectively). One particular preferred class of such proteins are the GTPase-like or ATPase-like binding proteins. GTPase proteins, e.g., EF-Tu, bind to a nucleic acid (in this case tRNA) and then are released when provided an energy source (e.g., GTP). The proteins may also require a co-factor for release (e.g., GAP) and thus release can be modulated by limiting supply of either the energy source or the co-factor. Detailed descriptions of GTPase-like proteins can be found in Scheffzek et al.(1997) *Science*, 277(18): 333–338, and Ahmadian et al. (1997) *Nature Structural Biology*, 4(9): 686–689).

Figure 6:
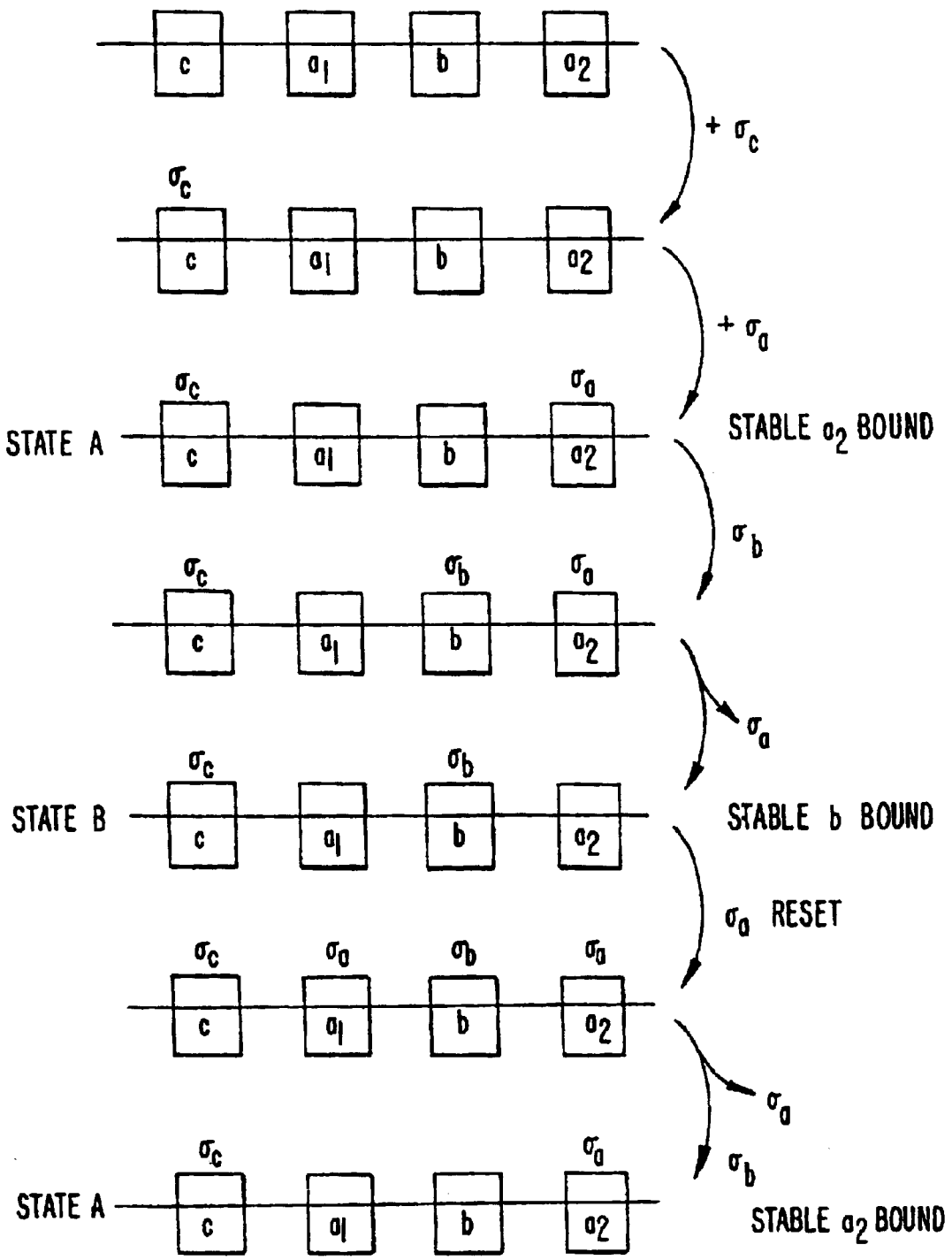

The GTPase-like proteins provide a convenient means for setting and resetting the flip-flop. Such a resettable flip-flop is illustrated in FIG. 6. This consists of a nucleic acid having 4 binding sites, designated c, $a_1$, b, and $a_2$. The site can be bound by $\sigma_x$ which is a nucleic acid binding protein. The $\sigma$ proteins are GTPase-like proteins that, when triggered, release the nucleic acid. The proteins also contain a GAP finger that can trigger the release of the adjacent a protein, but that cannot trigger its own release (see, Scheffzek et al. supra. and Ahmadian et al. supra.)

The $\sigma_c$ protein then binds site c and because of its GAP finger, causes the removal of any $\sigma_a$. Thus, when the flip-flop is contacted with $\sigma_a$ the $\sigma_a$ only remains bound at site $a_2$. The flip-slop is thus stable at site $a_2$. To switch its state, the flip-flop is contacted with $\sigma_b$ that binds at site b causing the removal of $\sigma_a$ and leaving the flip-flop stably bound at site b, the second state of the flip-flop. The flip-flop can be reset to state a by contacting it with $\sigma_a$ which binds to sites $a_1$ and $a_2$. When $a_1$ is bound by $\sigma a$ it will cause the release of $\sigma_b$. Although $\sigma_a$ may only be bound transiently, the free $\sigma_2$ in solution will ensure that the site is occupied long enough to cause the displacement of $\sigma_b$. This leaves the flip-flop reset to state a, with site $a_2$ bound by $\sigma_a$. The cycle can be repeated indefinitely.

It will be appreciated that non-naturally occurring releasable proteins can be obtained by routine selection procedures. For example, the EF-Tu protein (or other binding proteins, e.g., restriction nucleases) can be routinely mutagenized and expressed on the surface of a filamentous phage in a "phage display library" (see, e.g., Marks et al. (1991) *J. Mol. Biol.*, 222: 581–597, Vaughn et al. (1996) Nature Vaughn et al. (1996) *Nature Biotechnology*, 14(3): 309–314, and the like).

Good releasable proteins can then be routinely identified by screening the library for phage (clones) that bind to a nucleic acid bearing appropriate binding sites and that release in the presence of an energy source (GTP) with or without a cofactor (e.g., GAP). Subsequent rounds of mutagenesis and selection can produce binding proteins that show high affinity and specificity and efficient release in a manner analogous to the enrichment and selection for antibodies having high specificity and affinity (see, e.g., Vaughn et al. supra, Marks et al. supra.).

3) Construction of Nucleic Acid.

The underlying nucleic acid can be produced according to any of a number of methods well known to those of skill in the art. In one embodiment, the nucleic acid can be an isolated naturally occurring nucleic acid (e.g., a Fis binding site containing segment from *E coli*). However, in a preferred embodiment, the nucleic acid is created de novo, e.g. through chemical synthesis.

Nucleic acids (e.g., oligonucleotides) are typically chemically synthesized according to the solid phase phosphoramidite triester method described by Beaucage and Caruthers (1981), *Tetrahedron Letts.*, 22(20):1859–1862, e.g. using an automated synthesizer, as described in Needham-VanDevanter et al (1984) *Nucleic Acids Res.*, 12:6159–6168. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

It will be appreciated that chemically synthesized oligonucleotides are single-stranded. Double stranded nucleic acids (e.g. for binding proteins such as Fis) can be produced by synthesizing the complementary oligonucleotide and then annealing the two fragments in a simple hybridization reaction according to methods well known to those of skill in the art (see, e.g., Sambrook, et al., *Molecular Cloning A Laboratory Manual* (2nd Ed.), Vol. 1–3, Cold Spring Harbor Laboratory, Cold Spring Harbor, N.Y., 1989).

Alternatively a single oligonucleotide can be synthesized having complementary regions. Under appropriate hybridization conditions the oligonucleotide will self-hybridize forming a hairpin having a double stranded region containing the desired binding site (see, e.g., Example 2).

4) Construction of Binding Protein.

a) Isolation

The nucleic acid binding protein can be isolated from natural sources, mutagenized from isolated proteins or synthesized de novo. Means of isolating naturally occurring nucleic acid binding proteins are well known to those of skill in the art. Such methods include but are not limited to well known protein purification methods including ammonium sulfate precipitation, affinity columns, column chromatography, gel electrophoresis and the like (see, generally, R. Scopes, (1982) *Protein Purification*, Springer-Verlag, N.Y.; Deutscher (1990) *Methods in Enzymology Vol. 182: Guide to Protein Purification.*, Academic Press, Inc. N.Y.).

Where the binding protein binds reversibly, nucleic acid affinity columns bearing a nucleic acid having a binding site specific for the protein of interest can be used to affinity purify the protein. Alternatively the protein can be recombinantly expressed with a HIS-Tag and purified using $Ni^{2+}$/NTA chromatography.

b) Chemical Synthesis

In another embodiment, the binding protein can be chemically synthesized using standard chemical peptide synthesis techniques. Where the desired subsequences are relatively short the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond. This is typically accomplished using the same chemistry (e.g., Fmoc, Tboc) used to couple single amino acids in commercial peptide synthesizers.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, Solid-Phase Peplide Synthesis; pp. 3–284 in *The Peptides: Analysis, Synthesis, Biology. Vol. 2: Special Methods in Peptide Synthesis, Part A.*, Merrifield, et al. (1963) *J. Am. Chem. Soc.*, 85: 2149–2156, and Stewart et at. (1984) *Solid Phase Peplide Synthesis*, 2nd ed. Pierce Chem. Co., Rockford, Ill.

c) Recombinant Expression,

In a preferred embodiment, the binding proteins are synthesized using recombinant DNA methodology. Generally this involves creating a DNA sequence that encodes the binding protein, placing the DNA in an expression cassette under the control of a particular promoter, expressing the protein in a host, isolating the expressed protein and, if required, renaturing the protein.

DNA encoding binding proteins or subsequences of this invention can be prepared by any suitable method as described above, including, for example, cloning and restriction of appropriate sequences or direct chemical synthesis by methods such as the phosphotriester method of Narang et al. (1979) *Meth. Enyzmol.* 68: 90–99; the phosphodiester method of Brown et al. (1979) *Meth. Enzymol.* 68: 109–151; the diethylphosphoramidite method of Beaucage et al. (1981) *Tetra. Lett.*, 22: 1859–1862; and the solid support method of U.S. Pat. No. 4,458,066.

The amino acid and nucleic acid sequences of literally hundreds of nucleic acid binding proteins are well known to those of skill in the art. Thus, for example, the amino acid sequence of Fis (*E. coli* Factor for Inversion Stimulation) is found at Swiss-Prot entry P11028.

The nucleic acid sequences encoding the desired binding protein(s) may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant binding proteins can be purified according to standard procedures of the art as described above.

One of skill in the art would recognize that after chemical synthesis, biological expression, or purification, the binding protein(s) may possess a conformation substantially different than the conformations of the native polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.*, 268: 14065–14070; Kreitman and Pastan (1993) Bioconjug. Chem., 4:581–585; anti Buchner, et al., (1992) *Anal. Biochem.*, 205: 263–270). Debinski et al., for example, describes the denaturation and reduction of inclusion body proteins in guanidine-DTE. The protein is then refolded in a redox buffer containing oxidized glutathione and L-arginine.

One of skill would recognize that modifications ran be made to the binding proteins without diminishing their biological activity. Some modifications may be made to facilitate the cloning, expression, or incorporation of the targeting molecule into a fission protein. Such modifications are well known to those of skill in the art and include, for example, a methionine added at the amino terminus to provide an initiation site, or additional amino acids (e.g., poly His) placed on either terminus to create conveniently located restriction sites, termination codons or purification sequences.

It is also recognized that a large number of binding proteins have been cloned and can be reproduced using standard recombinant DNA methodology. In addition some (particularly normal and modified restriction enzymes) are commercially available.

B) Binding Site Selectors/Modulators/Blockers.

It was noted above, that the binding of binding proteins to particular binding sites can be controlled by the use of various selectors (also referred to as modulators or blockers). The selector can be a binding protein or any other moiety that selectively blocks the binding site with which it is associated. Thus, the selector can be a modified restriction endonuclease (e.g., an EcoRI mutated to eliminate the cleavage function, see, e.g., King et al. (1989) *J. Biol. Chem.*, 264(20): 11807–11815 and Wright et al. (1989) *J. Biol. Chem.*, 264(20) 11816–11821) that binds to, but does not cleave the underlying nucleic acid. The selector could also be a chemical that selectively modifies the underlying nucleic acid:(e.g., base modification, thymidine dimerization, etc.) to prevent attachment of the binding protein. Other possible selectors include nucleic acids (e.g., antisense molecules) peptide nucleic acids, streptavidin, avidin, and the like.

Selectors can also include photocleavable blockers. Such blockers remain attached to the substrate molecule until they are exposed to light of a particular wavelength. Once exposed they cleave thereby unblocking the site and allowing the binding of the signal molecule. This permits the use of an optical signal to set the state of various elements of the logic circuit. Similarly the use of fluorescent readout methods, described above, provides an optical output. Thus, both input and output of the system can be effected by optical signals.

This is convenient for computational input and output. It is noted that where the computational elements are components of "logic cassettes", this also provides optical control over gene expression. It is expected that such optical control systems will prove most efficacious in vitro.

Photocleavable blockers are well known to those of skill in the art and include, but are not limited to NVOC, MeNPOC, Dimethoxybenzoinyl, or DDZ. (see,e.g., U.S. Pat. Nos. 5,679,773, 5,639,603, 5,525,735, 5,709,848, 5,556,961, and 5,550,215).

C) Tethered Activator(s).

It was explained above that tethering a gene activator (e.g., Gal4) to an "output" nucleic acid binding site provides a mechanism for coupling the output of one logic element (e.g. flip-flop or gate) to another. It has been demonstrated that a number of gene activators will activate a gene even in the absence of the native response element when the activator is tethered to the underlying nucleic acid. This was first demonstrated by Ptashne who showed that a nucleic acid binding protein (an *Escherichia coli* repressor protein; LexA) fused to an activator (a Saccharomyces cerevisiae transcriptional activator; Gal4) activated transcription of a gene if and only if a protein binding site (the lexA operator) is present near the transcription start site (see Ptashne (1985) *Cell*, 43(3): 729–736, and Farrell et al. (1996) *Genes Dev.*, 10(18): 23 59–2367).

Other tethered activators have been made, for example, by fusing a heterologous DNA binding domain (Gal4) to yeast ADA2 protein (see, Silverman et al. (1993) *Proc. Natl. Acad Sci. USA*, 91: 11665–11668). Similarly, fusion of a heterologous DNA binding domain to the amino terminus of CREB-binding protein allowed the chimeric protein to function as a protein kinase A-regulated transcriptional activator. (Chrivia et al. (1993) *Nature*, 365: 855–859). Similarly, the BOB. I/OBF.I B cell-restricted cofactors fused to GAL4 DNA binding domain can efficiently activate octamer-dependent promoters in fibroblasts (see, Pfisterer et al. (1995) *Biol. Chem.*, 270(50): 29870–29880). Other gene activators and repressors are well known to those of skill in the art.

When the binding proteins are joined by a linker, the length of the linker is selected so that when one end of the tethered construct is bound to its cognate target (e.g., the output of a logic gate), the binding protein at the opposite end is brought into close proximity (e.g., juxtaposed) to transcription initiation site it is designed to interact with.

Methods of linking proteins are well known to those-of skill in the art. Typically the binding and activator proteins can be linked by a chemically conjugated linker or alternatively, can be expressed as a fusion protein in which the two binding proteins are linked by a polypeptide.

Means of chemically conjugating molecules are well known to those of skill (see, for example, Chapter 4 in *Monoclonal Antibodies: Principles and Applications*, Birch and Lennox, eds. John Wiley & Sons, Inc. N.Y. (1995) which describes conjugation of antibodies to anticancer drugs, labels including radio labels, enzymes, and the like). Proteins contain variety of functional groups, e.g., carboxylic acid (COOH) or free amine ($—NH_2$) groups, which are available for reaction with a suitable functional group on a suitable linker bind the protein thereto.

Alternatively, the binding protein(s) may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the binding proteins. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. The linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form the desired tethered construct. Alternatively, derivatization may involve chemical treatment of the binding protein, e.g., glycol cleavage of a sugar moiety attached to the protein with periodate to generate free aldehyde groups. The free aldehyde groups on the protein may be reacted with free amine or hydrazine groups on an agent to bind the agent thereto. (See U.S. Pat. No. 4,671,958). Procedures for generation of free sulfhydryl groups on polypeptides are also known (See U.S. Pat. No. 4,659,839).

Many procedures and linker molecules for attachment of various proteins are known. See, for example, European Patent Application No. 188,256; U.S. Pat. Nos. 4,671,958, 4,659,839, 4,414,148, 4,699,784; 4,680,338; 4,569,789; and 4,589,071; and Berlinghaus et al. *Cancer Res.* 47: 4071–4075 (1987). Such linkers are widely used in the production of immunotoxins and can be found, for example in "Monoclonal Antibody-Toxin Conjugates: Aiming the Magic Bullet," Thorpe et al., *Monoclonal Antibodies in Clinical Medicine*, Academic Press, pp. 168–190 (1982), Waldmann, *Science*, 252: 1657 (1991), U.S. Pat. Nos. 4,545, 985 and 4,894,443.

In a preferred embodiment, the tethered construct is expressed as a recombinant fusion protein (i.e. the two binding domains are joined by a polypeptide linkage). This basically involves providing an expression cassette encoding both binding proteins, and if necessary a linker, transfecting a cell with the expression cassette and thereby expressing the tethered construct. Methods of expressing heterologous nucleic acids are described above in the discussion of recombinant expression of binding proteins and the recombinant expression of binding protein—activator fusion proteins is well known (Silverman et al. (1993) *Proc. Natl. Acad Sci. USA*, 91: 11665–11668, Chrivia et al. (1993) *Nature*, 365: 855–859, and Pfisterer et al. (1995) *Biol. Chem.*, 270(50): 29870–29880).

It will be appreciated that the binding proteins attached to the activators need not be full-length binding proteins. To the contrary, in a preferred embodiment, only the nucleic acid binding domain will be attached to the termini of the tethered construct.

III) Solution Phase Solid Phase and In vivo Systems

A) Ex vivo Systems.

Where the logic constructs (e.g. flip-flops and/or gates) of this invention are used for computation and/or affinity chromatography, the application will preferentially be performed ex vivo. In this context, the computational elements may be utilized in solution and/or they may be attached to a solid support. When attached to, a solid support the computation and/or affinity assay is effectively run in the solid phase. The term "solid support" refers to a solid material which may be functionalized to permit the coupling of the nucleic acid or the binding protein to the surface. However many solid supports (e.g., nitrocellulose) do not require such derivatization. Any material to which the nucleic acid or binding protein can be attached and which is stable to reagents with which it will be contacted is suitable. Solid support materials include, but are not limited to, polacryloylmorpholide, metals, plane glass, silica, controlled pore glass (CPG), polystyrene, polystyrene/latex, and carboxyl modified teflon.

In one embodiment, the various logic elements can be arranged in arrays. Methods of making single or double stranded nucleic acid arrays are well known to those of skill in the art (see. e.g., U.S. Pat. No. 5,143,854 and PCT patent publication No. WO 90/15070).

In solution or solid phase, the input signal proteins, output signal proteins, blockers, and tethered construct(s) can be added simultaneously or sequentially as needed. Similarly, readout is performed by any of a number of routine means as described above.

Gene expression may also be performed ex vivo in extracted natural, or synthetic expression systems. Such systems, typically include a buffer, and all of the elements necessary to transcribe and translate a gene (e.g., ATP, Mg, ribozymes, nucleotide triphosphates, etc.).

Alternatively, the gates of this invention could be added to bioreactors to simultaneously assay and modulate the reactor environment. Thus, for example, the OR gate described above when added to a bioreactor will bind one or more analytes if they are present in the reactor system. Such binding will set the output HIGH. The HIGH output binding site can then bind a third analyte in the bioreactor rendering it less available or unavailable to the organisms growing therein.

B) In vivo Systems

In another embodiment, the logic controls of this invention can be used for regulation of gene expression. As explained above, a cell can be transfected with one or more "logic cassettes"; expression cassettes comprising nucleic acids that encode one or more genes whose expression is under the control of a logic element (e.g., one or more gates and/or flip-flops) of this invention.

The logic cassette can be transfected into a cell using standard vectors as described above. The logic cassette can additionally encode one or more binding proteins and/or one or more tethered constructs. Alternatively, the binding proteins can be endogenously expressed proteins or can be provided by other expression or logic cassettes. Similarly, the tethered constructs can also be expressed by one or more separate expression cassettes or logic cassettes.

IV. Other Substrate-based Logic Elements

While the examples provided herein demonstrate logic elements (flip-flops and gates) that use nucleic acid binding sites, other substrates are suitable as long as they can be specifically bound. Such substrates include, but are not limited to proteins, glycoproteins, sugars, and the like. Proteins provide a particularly preferred alternative substrate. It is well known that a single protein can display a wide variety of different epitopes each of which is specifically bound by a particular antibody (e.g. a monoclonal antibody or antibody fragment Fv, Fab', etc., or single chain Fv, etc.). Moreover it is also known that epitopes can be juxtaposed such that they cannot be simultaneously bound by their respective antibodies. This principle forms the basis of epitope mapping.

Thus, a protein that displays two epitopes for which antibody binding is mutually exclusive forms the basis for a protein substrate flip-flop. Similarly, sugars or glycoproteins can form a substrate for mutually exclusive lectin binding according to the same principle.

V. Kits for Molecular Computation and/or Complex Expression Control

This invention also provides kits for molecular computation and/or for the regulation of gene expression. The kits comprise one or more containers containing the logic elements (e.g., flip-flops, gates, logic cassettes) of this invention. The container(s) may simply contain the underlying nucleic acid or the combined nucleic acid and/or signal polypeptide and/or one or more tethered constructs. Where the kit is designed for ex vivo application, the various elements may be provided attached to one or more surfaces of a solid support (e.g. a 96 well microtiter plate).

The kit may also optionally include reagents, buffers, fluorescent labels, etc., for the practice of one of the methods described herein.

The kits may optionally include instructional materials containing directions (i.e., protocols) providing for the use of the logic elements (flip-flops, gates, etc.) of this invention in molecular computation systems, gene control, and the like. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Overlapping Fis Sites 7 or 11 Base Pairs Apart are not Bound Simultaneously

In this Example, information theory was used to predict Fis (Factor for Inversion Stimulation) binding sites in *Escherichia coli* DNAs. These predictions have been confirmed by previously existing DNase I footprints or by gel mobility shift experiments. In many diverse genetic systems including six site-specific inversion regions, λ att, dif, nrd, ndh and the fis promoter, Fis sites are also predicted to be 7 or 11 base pairs apart. These overlapping Fis sites are frequently coincident with binding sites of other proteins, suggesting that Fis can block access to DNA. The structure of the Fis sequence logo, molecular modeling and gel mobility shift experiments all indicate that Fis sites separated by 7 or 11 bases are bound antagonistically. Two overlapping Fis sites separated by 11 base pairs also occur in the *E. coli* origin of chromosomal replication (oriC). The data presented herein suggest that both sites bind Fis and that they compete for binding to create two distinguishable molecular states in vitro. Since only one of the two overlapping Fis sites can be bound by Fis at a time, the structure is a molecular flip-flop. These two Fis sites are precisely positioned between two DnaA sites in oriC, suggesting that the flip-flop directs alternative firing of replication complexes in opposite directions.

Fis is a well characterized site-specific DNA binding protein. When *Escherichia coli* encounters a rich nutritional medium, the number of Fis molecules increases from nearly zero to 25,000 to 50,000 dimers per cell (Ball et al. (1992) *J. Bact.* 174: 8043–8056). Estimates of the number of Fis sites in the *E. coli* genome based on the average information in Fis sites give a similar number, indicating that most of these molecules are controlling genetic systems throughout the genome (Hengen et al. (1997) *Nucl. Acids Res.*, 25(24): 4994–5002). Fis is known to bend DNA and it is involved in many site-specific recombination systems. In addition, it autoregulates its own promoter and activates other promoters (Johnson & Simon (1987) *Trends in Genetics*, 3: 262–267; Finkel & Johnson (1992) *Molec. Microb.*, 6: 3257–3265; Finkel & Johnson (1992) *Molec. Microb.*, 6: 1023).

Information analysis of Fis binding sites and their surrounding sequences has revealed previously unidentified sites adjacent to known ones (Hengen et al. (1997) supra). It was observed that pairs of Fis sites are often separated by 7 or 11 bases in many genetic systems. These Fis sites often overlap the binding sites of other proteins in significant places such as the Xis site of λ att (Schneider(1997) *Nucl. Acids. Res.*, 25: 4408–4415). To understand the significance of these pairs we sought to determine whether Fis binds cooperatively or antagonistically at the adjacent sites. In this study we show that in an artificial DNA construct the sites cannot be bound simultaneously and therefore act as a molecular flip-flop.

DNA replication starts at 83 minutes on the *E. coli* chromosome at a locus called oriC. Bidirectional replication starting at oriC is completed in the terminus region half way around the chromosome. Replication is dependent on the DnaA protein which binds at 5 sites in oriC. Using sequence walkers (Schneider (1997) *Nucl. Acids. Res.*, 25: 4408–4415), we observed that there are likely to be two Fis sites wedged precisely between two of the DnaA sites.

Results and Discussion

Self-competition Between Natural Fis Sites.

When we searched DNA sequences for Fis sites using an information theory based weight matrix, we observed Fis sites spaced 11 base pairs apart in hin gin, and min (see FIG. 5 in (Hengen et al., 1997, supra.). Since B-form DNA twists every 10.6 base pairs, the sites should be on the same side of the DNA. While it is conceivable that two adjacent proteins can bind simultaneously by a subtle interleaving of their DNA contacts, it seems more likely that they will compete for binding in the major groove since after an 11 base: shift the sequence logo shows that the predominant C at −7 corresponds to the G at +4 and the C at −4 corresponds to the C at +7 (downward pointing arrows in FIG. 7). Competition between these internally (FIG. 7) redundant patterns (Schneider & Mastronarde (1996) *Discrete Applied Mathematics*, 71: 259–268) would allow Fis to change its site of DNA bending and perhaps this is important for inversion.

In contrast, in the P1 cin, P7 cin and *E. coli* e 14 pin sites, the spacing between pairs is only 7 bases, which would place the Fis dimers 122° apart on B-DNA (360°−360° per turn×7 bases/10.6 bases per turn=122°). After a 7 base shift, the sequence logo shows that the G at −7 would match the A/T of the minor groove on the opposite face of the DNA at coordinate 0, while the C/T at −4 would match the T/C at +3 and the A/G at −3 would match the C/A at +4 (up arrows in FIG. 7). This allows for the possibility that the two proteins bind at the same time, which might also be important to the function of these regions.

To investigate the consequences of two Fis molecules binding to nearby sites, we constructed 3 dimensional models (Schneider (1997) *Nucl. Acids Res.*, 25: 4408–4415). We found that two Fis proteins bound to sites separated by 11 base pairs might strongly interpenetrate. In contrast, a 7 base pair separation might only have a minimal van der Waals force conflict between the two central D helices. This might be accommodated for by flexibility of the DNA-protein complex, given that there is some uncertainty as to how Fis binds DNA. We thought that 11-base separated Fis molecules would compete for binding but that a 7-base separation might allow simultaneous binding.

These ideas are supported by the preliminary observation that synthetic DNA containing either the hin proximal or medial Fis sites are bound by Fis in electrophoretic mobility gel shift assays (Hengen et al.(1997) supra.). When these overlapping sites were together on the same fragment with a spacing of 11 bases only one band shift was observed, suggesting that only one of the sites can be bound at a time. To test whether this is the case requires using high concentrations of Fis and strong Fis sites to ensure that both sites would be bound if that were possible.

Test of the 7-11 Alternation Model

To determine whether overlapping Fis sites can be simultaneously bound by Fis, we synthesized strong Fis sites that overlap by either 7 or 11 base pairs (FIGS. 8*a*, 8*b*) or that were separated by 23 base pairs (FIG. 7*c*) and tested their properties by gel shift. Neither the 11 nor the 7 overlapping sites showed a doubly-shifted band, even at an extremely high Fis/DNA ratio and with exceptionally strong (>12 bits) Fis binding sites (FIG. 9), suggesting that only one Fis molecule could bind to each DNA fragment. The DNA fragment with two Fis sites separated by 23 base pairs did double shift, demonstrating that well separated Fis sites can cause two distinct band shifts (FIG. 9). However, Fis can create a ladder on non-specific sequences (Betermier et al. (1994) *Biochimie*, 76: 958–967), and this might account for the double-shifts. Under our conditions with short DNAs, a non-specific (all positions<1 bit) 66 bp DNA fragment barely shifted at high Fis concentration (data not shown) so the secondary shifts were not from non-specific binding. These results demonstrate that Fis sites separated by 7 or 11 bases cannot be bound simultaneously. We could not exclude the possibility that the single-shifted bands at high concentration of Fis contain two molecules of Fis per DNA as a complex that runs exactly as a DNA bound by one Fis molecule, but this seems highly unlikely given the sensitivity of gel shifts to molecular weight changes and the results for the 23 base separated DNA.

A second Fis molecule might be blocked by direct steric hindrance, but it is also possible for the first protein to distort the DNA enough to eliminate or occlude the second site. If a distortion mechanism is used, it remains possible that two weak Fis sites could be bound simultaneously. Further, the 7 base overlapped sites may be simultaneously bound at lower temperature, since low thermal agitation might allow binding despite some mechanical strain. Finally, superhelical DNA and other conditions might allow simultaneous binding.

Fis Switching: Genetic Implications of the 7–11 Flip-flop Model

The tyrT promoter has three Fis sites separated by 20 and 31 base pairs, as in our 23 base pair separated control experiment (FIG. 8 and FIG. 9). The separation in tyrT is sufficient for three Fis dimers to simultaneously position themselves on the same face of the DNA to cooperatively bind a $\sigma^{70}$ subunit and activate transcription of stable RNA promoters (Muskhelishvili et al. (1995) *EMBO J.*, 14: 1446–1452). In addition to this activation mechanism, which is based on separated sites, Fis may also have evolved another control mechanism that uses overlapping sites.

When we scanned our Fis individual information model across various sequences, we discovered 7 and 11 spacings at inversion regions, the fis, nrd, and ndh promoters; and at dif *E. coli* oriC and λ att (Hengen et al., 1997 supra.; Schneider (1997) *Nucleic Acids Res.*, 25: 44084415). In the latter three systems, Fis sites overlap binding sites of other proteins in significant places, so we do not think that Fis sites appear at this spacing merely because of the internal redundancy of the site. For example, scanning with the Fis weight matrix reveals two Fis sites previously identified in oriC at coordinates 202 and 213 (Roth et al. (1994) *Biochimie*, 76: 917–923). Footprinting data from two different groups show protection covering one, the other and both sites (FIG. 10). The two Fis sites fit. exactly between the R2 and R3 DnaA sites and have similar individual information contents, suggesting that their binding energies are similar, so in the absence of other effects Fis could occupy them for nearly equal fractions of the time as a flip-flop. Binding by DnaA and by Fis are mutually exclusive (Gille et al. (1991) *Nucl. Acids. Res.*, 19: 4167–4172), implying that the position of a Fis-induced DNA bend could be controlled by DnaA and the binding of DnaA could be controlled by Fis. During nutritional upshifts when there is a high Fis concentration (Ball et al. (1992) supra:), occupancy of one Fis site should ensure only one DnaA site is available at a time. Since absence of Fis leads to asynchronous replication (Boye et al. (1982) In *DNA Replication and the Cell Cycle*, Fanning Knippers and Winnacker eds., vol. 43: 15–26, Springer-Verlag, Berlin), this flip-flop right control alternative firing of replication complexes in opposite directions.

Closely spaced sites are often bound cooperatively, as in the classical example of T4 gene 32 autogenous regulation (Miller et al. (1994) In *Molecular Biology of Bacteriophage T4*, Karam et al., ed. pp. 193–205, *American Soc. Microbiol.*, Washington, D.C.). In contrast, Fis represents the unusual situation where a protein competes with itself by binding at overlapping positions. Self-occlusion has been observed in artificial constructs, where one ribosome is apparently blocked by the presence of another ribosome bound nearby (Barrick et al. (1994) *Nucl. Acids. Res.*, 22: 1287–1295. Likewise, in ColE1 and ColE7, a pair of LexA sites may be competing with each other for LexA binding (Ebina et al. (1983) *J. Biol. Chem.*, 258: 13258–13261); Lu & Chak (1996) *Mol. Gen. Genet.*, 251: 407–411).

The same pair of LexA sites in ColE7 may also compete with a 9.1 bit Fis site immediately upstream, and all three of these sit adjacent to two overlapping IHF sites immediately downstream. This interplay of factors may be typical of more complex flip-flop mechanisms. For example, as many as five Fis sites are likely to be in λ att. Two of these are spaced 11 base pairs apart, with one of them overlapping an Xis site (Schneider (1997) *Nucl. Acids. Res.*, 25: 4408–4415).

The positioning of Fis binding sites relative to one another and to the binding sites of other proteins therefore appears to be key for the ability of Fis to perform many diverse functions. Fis has evolved a transcriptional activation mode in which sites are on the same face of the DNA and are sufficiently apart to be bound simultaneously. Fis may also have specifically evolved to allow for two competitive binding modes. When the sites are on the same face of DNA (11 bp apart), a single Fis molecule could disengage and rebind to move the bend location between two possible places without changing the overall direction of the DNA. When sites are on nearly opposite faces (7 bp apart), Fis would cause the bend direction to change by 122°. How these cogs fit into the larger picture of pleiotropic Fis functions remains to be determined.

This Example demonstrates that adjacent Fis sites can have two distinct binding modes in which Fis competes with itself for binding and therefore acts as a molecular flip-flop.

Materials and Methods

Sequence Analysis Programs

Delila system programs were used for handling sequences and information calculations (Schneider et al. (1982) *Nucl. Acids Res.*, 10: 3013–3024; Schneider et al. (1984) *Nucl. Acids Res.*, 12: 129–140; Schneider et al. (1986) *J. Mol. Biol.*, 188: 415–431; Schneider & Stephens (1990) *Nucl. Acids. Res.*, 18: 6097–6100; Stephens & Schneider (1992) *J. Mol. Biol.*, 228: 1124–1136; Schneider (1997) *J. Theoret Biol.*, 189(4): 427–441; Schneider (1997) *Nucl. Acids Res.*, 25: 4408–4415). Figures were generated automatically from raw GenBank data using Delila and UNIX script programs.

Design of Fis Binding Experiments

Synthetic DNAs containing strong Fis sites separated by 11 and 1 base pairs were designed by selecting from the most frequent bases at each position in the Fis sequence logo (Hengen et al. (1997) supra.). These were then merged with the same sequence shifted by 11 or 7 base pairs by comparing the $R_{iw}(b,l)$ values for various choices. (Note: the consensus sequence of the early model we used was TTTG (G/C)TCA AAATTTGA(G/C)C AAA (SEQ ID NO:1) which differs from that of the logo.) Five extra bases were added to the ends based on the natural sequences around the hin proximal and medial sites for the overlap 11 oligo, and the sequences around cin external and proximal sites were used for the overlap 7 oligo (Hengen et al. (1997) supra.). The DNAs were made self complementary (FIGS. 8a, 8b). Sites separated by 23 bases were created starting with the 11 base separated DNA and duplicating the central overlap region. A BamHI site was also inserted and the DNA was flanked by EcoRI sites (FIG. 10c). Oligonucleotides were synthesized with biotin on the 5' end and gel purified (Oligos Etc., Wilsonville, Oreg., USA). To ensure thorough annealing, they were heated to 90° C. for 10 minutes, and slowly cooled to room temperature. The annealed products were electrophoresed through an 8% (w/v) polyacrylamide gel, and the bands corresponding to the linear duplex DNA of the correct size were sliced from the gel. DNA was recovered by electroelution and extracted with isoamyl alcohol to remove ethidium bromideon-specific control DNA was composed of the two 66 bp hinFI fragments from bacteriophage ϕX174 (Life Technologies, Inc.). Gel mobility shift experiments were performed as described (Hengen et al. (1997) supra.).

Example 2

Readout of a Fis/DNA Flip-Flop

A single very long nucleic acid (SEQ ID NO:15) is synthesized having a sequence in the center that causes a hairpin loop to form rapidly (see, FIG. 11). The entire DNA can then be dissolved in a buffer heated and cooled thereby forming double stranded DNA. This guarantees that the complementary strands are equimolar and there is't any single-stranded DNA present in the mixture.

The nucleic acid is designed so that it form the oriC site-on hairpin formation and a biotin is attached (via a 19 atom linker) to the T's at either position 77 or 78.

Fis is put in with the hairpin loop DNA. The Fis is expected to bind to the two positions (18 and 29 in FIG. 11, note that the Fis sites at 87 and 98 are the same ones on the other strand of the DNA). Streptavidin is then added.

When a Fis molecule is bound at position 18, the streptavidin can also bind and one should see a high band shift consisting of DNA, Fis and streptavidin. When a Fis molecule is bound a position 29, it will block streptavidin and only DNA and Fis will be present so the band will be lower on the gel. Visiblity of both bands will indicate that in solution both binding sites form.

Appropriate controls include knockouts of each binding site individually and of both sites. Experiments include just DNA, DNA+Fis, DNA+Fis+Streptavidin, and DNA+Streptavidin+Fis to see that the order of addition affects the results. The only time that there should be two bands is the DNA+Fis+Streptavidin order of addition when both Fis sites exist.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A system comprising
an isolated nucleic acid having a length of at least 5 base pairs and having a nucleotide sequence that comprises a first protein binding site and a second protein binding site, where said first and second protein binding sites specifically bind the same nucleic acid binding protein, and where said first and second protein binding sites are spaced in proximity to each other such that:
when said first protein binding site is specifically bound by the nucleic acid binding protein, said second binding site cannot be bound by a second molecule of the protein that otherwise specifically recognizes and binds said second binding site; and
when said second binding site is specifically bound by the nucleic acid binding protein, said first binding site cannot be bound by a second molecule of the protein that otherwise specifically recognizes and binds said first binding site; and
the nucleic acid binding protein that specifically binds said first protein binding site or said second protein binding site.

2. The system of claim 1, wherein said nucleic acid is a double-stranded nucleic acid.

3. The system of claim 1, wherein said nucleic acid is a deoxyribonucleic acid (DNA).

4. The system of claim 1, wherein said first binding site and said second binding site have the same nucleotide sequence.

5. The system of claim 1, wherein said first binding site and said second binding site have the nucleotide sequence of SEQ ID NO: 1.

6. The system of claim 1, wherein said nucleic acid binding protein is selected from the group consisting of Fis, and Tus.

7. The system of claim 1, wherein said nucleic acid binding protein is EF-Tu.

8. The system of claim 1, wherein said first binding site is within 20 nucleotides of said second binding site.

9. The system of claim 1, wherein said first binding site is within 11 nucleotides of said second binding site.

10. The system of claim 8, wherein said first binding site has a strength of at least 2.4 bits as determined by individual information theory.

11. The system of claim 1, wherein there is a difference in strength between said first protein binding site and said second protein binding site of more than 0 bits as determined by individual information theory.

12. The composition of claim 1, further comprising a third protein binding site wherein said third site is in proximity to said first protein binding site or to said second protein binding site such that specific binding of said third binding site with a protein precludes specific protein binding of said first or said second protein binding sites.

13. The system of claim 1, wherein:
said first-protein binding site is a Fis binding site;
said second protein binding site is a Fis binding site; and
said binding sites are separated from each other by less than 12 nucleotide base pairs.

14. The system of claim 13, wherein said nucleic acid is a deoxyribonucleic acid comprising the sequence of SEQ ID NO: 2 or SEQ ID NO: 3.

15. A composition comprising, an isolated nucleic acid having a length of at least 5 base pairs and having a nucleotide sequence that comprises a first protein binding site, a second protein binding site, and a third protein binding site where said protein binding sites are spaced in proximity to each other such that:
when either said first protein binding site or said third protein binding is specifically bound by a nucleic acid binding protein, said second binding site cannot be bound by a nucleic acid binding protein that otherwise specifically recognizes and binds said second binding site; and
where said first protein binding site and said third protein binding site can simultaneously be specifically bound by a nucleic acid binding protein.

16. The composition of claim 15, wherein said first protein binding site or said third protein binding site is bound by a nucleic acid binding protein.

17. The composition of claim 15, wherein said third protein binding site is bound by a nucleic acid binding protein.

18. The composition of claim 17, wherein said binding protein is attached to a gene transactivator.

19. The composition of claim 18, wherein said transactivator is a Gal4 transactivator.

20. The composition of claim 15, further comprising a gene or cDNA under the control of said transactivator.

21. The composition of claim 20, further comprising a gene or cDNA under the control of said transactivator.

22. The composition of claim 21, wherein said gene is a reporter gene.

23. The composition of claim 21, wherein said gene encodes a nucleic acid binding protein.

24. The composition of claim 15, wherein said nucleic acid is a double-stranded nucleic acid.

25. The composition of claim 15, wherein said nucleic acid is a deoxyribonucleic acid (DNA).

26. The composition of claim 15, wherein said first binding site and said third binding site have the same nucleotide sequence.

27. The composition of claim 15, wherein said first binding site or said second binding Site is specifically recognized and bound by a protein selected from the group consisting of Fis, and Tus.

28. The composition of claim 15, wherein said first binding site or said second binding site is bound by EF-tu.

29. The composition of claim 15, wherein said first binding site is within 20 nucleotides of said second binding site.

30. The composition of claim 15, wherein said first binding site is within 11 nucleotides of said second binding site.

31. The composition of claim 30, wherein said first binding site has a strength of at least 2.4 bits as determined by individual information theory.

32. The composition of claim 15, wherein the difference in strength between said first protein binding site and said second protein binding site is at least 0 bits as determined by individual information theory.

33. The composition of claim 1, wherein:
said first protein binding site is a Fis binding site;
said third protein binding site is a Fis binding site.

34. A composition for the storage of binary information, said composition comprising an isolated nucleic acid having a length of at least 3 base pairs and having a nucleotide sequence that encodes a first protein binding site and a second protein binding site, where said first and second protein binding sites specifically bind the same nucleic acid binding protein, and where said first and second protein binding sites are spaced in proximity to each other such that:
when said first protein binding site is specifically bound by the protein, said second binding site cannot be bound by a second molecule of the protein that otherwise specifically recognizes and binds said second binding site; and
when said second binding site is specifically bound by the protein, said first binding site cannot be bound by a second molecule of the protein that otherwise specifically recognizes and binds said first binding site; and
further comprising the nucleic acid binding protein bound to said first protein binding site or said second protein binding site.

35. The composition of claim 34, wherein said nucleic acid is a double-stranded nucleic acid.

36. The composition of claim 34, wherein said nucleic acid is a deoxyribonucleic acid (DNA).

37. The composition of claim 34, wherein said first binding site and said second binding site have the same nucleotide sequence.

38. The composition of claim 34, wherein said nucleic acid binding protein is selected from the group consisting of Fis, and Tus.

39. The composition of claim 34, wherein said first binding site is within 20 nucleotides of said second binding site.

40. The composition of claim 34, wherein said first binding site is within 11 nucleotides of said second binding site.

41. The composition of claim 40, wherein said first binding site has a strength of at least 2.4 bits as determined by individual information theory.

42. The composition of claim 34, wherein there is a difference in strength between said first protein binding site and said second protein binding site of more than 0 bits as determined by individual information theory.

43. The composition of claim 34, further comprising a third protein binding site wherein said third site is in proximity said first protein binding site or said second protein binding site such that specific binding, of said third binding site with a protein precludes specific protein binding of said first or said second protein binding sites.

44. The composition of claim 34, wherein:
said first protein binding site is a Fis binding site;
said second protein binding site is a Fis binding site;
and said binding sites are separated from each other by less than 12 nucleotide base pairs.

45. The composition of claim 44, wherein said nucleic acid is a deoxyribonucleic acid comprising the sequence of SEQ ID NO: 2 or SEQ ID NO: 3.

46. The composition of claim 34, wherein said binding protein is attached to a gene transactivator.

47. The composition of claim 46, wherein said transactivator is a Gal4 transactivator.

48. The composition of claim 46, further comprising a gene or cDNA under the control of said transactivator.

49. The composition of claim 48, wherein said gene is a reporter gene.

50. The composition of claim 48, wherein said gene encodes a nucleic acid binding protein.

51. A method of storing information, said method comprising the step of:
binding a nucleic acid binding protein to a first protein binding site on a nucleic acid, wherein said nucleic acid has a length of at least 3 base pairs and said nucleic acid comprises said first protein binding site and a second protein binding site, where said first and second protein binding sites specifically bind the same nucleic acid binding protein, and where said first and second protein binding sites are spaced in proximity to each other such that:
when said first protein binding site is specifically bound by the protein, said second binding site cannot be bound by a second molecule of the protein that otherwise specifically recognizes and binds said second binding site; and
when said second binding site is specifically bound by the protein, said first binding site cannot be bound by a second molecule of the protein that otherwise specifically recognizes and binds said first binding site.

52. The method of claim 51, further comprising the step of determining which binding site on said nucleic acid is bound by said binding protein.

53. The method of claim 51, wherein said nucleic acid is a double-stranded nucleic acid.

54. The method of claim 51, wherein said nucleic acid is a deoxyribonucleic acid (DNA).

55. The method of claim 51, wherein said first binding site and said second binding site have the same nucleotide sequence.

56. The method of claim 55, wherein said first binding site and said second binding site have the nucleotide sequence of SEQ ID NO: 1.

57. The method of claim 51, wherein said first binding site or said second binding site is specifically recognized and bound by a nucleic acid binding protein selected from the group consisting of Fis, EF-Tu, and Tus.

58. The method of claim 51, wherein said first binding site is within 20 nucleotides of said second binding site.

59. The method of claim 51, wherein said first binding site is within 11 nucleotides of said second binding site.

60. The method of claim 51, wherein said first binding site has a strength of at least 2.4 bits as determined by individual information theory.

61. The method of claim 51, wherein there is a difference in strength between said first protein binding site and said second protein binding site of more than 0 bits as determined by individual information theory.

62. The method of claim 51, wherein:

said first protein binding site is a Fis binding site;

said second protein binding site is a Fis binding site; and said binding sites are separated from each other by less than 12 nucleotide base pairs.

63. The system of claim 13, wherein said nucleic acid is a deoxyribonucleic acid comprising the sequence of SEQ ID NO: 2 or SEQ ID NO: 3.

64. A method of transforming binary information, said method comprising the steps of:

(i) binding a nucleic acid binding protein to an input protein binding site on a first nucleic acid; and (ii) determining whether or not a nucleic acid binding protein can bind to an output protein binding site on a second nucleic acid;

wherein said first nucleic acid is an isolated nucleic acid having a length of at least 5 base pairs and having a nucleotide sequence that encodes a first protein binding site, a second protein binding site, and a third protein binding site where said protein binding sites are spaced in proximity to each other such that:

when either said first protein binding site or said third protein binding is specifically bound by a nucleic acid binding protein, said second binding site cannot be bound by a nucleic acid binding protein that otherwise specifically recognizes and binds said second binding site; and where said first protein binding site and said third protein binding site can simultaneously be specifically bound by a nucleic acid binding protein.

65. The method of claim 64, wherein said first nucleic acid and said second nucleic acid are the same nucleic acid.

* * * * *

SEQUENCE LISTING

```
<160> NUMBER OF SEQ ID NOS: 19

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:consensus
      sequence of early model of Factor for Inversion
      Stimulation (Fis) binding site

<400> SEQUENCE: 1
ttgstcaaaa tttgascaaa                                              20

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence:paired
      Factor for Inversion Stimulation (Fis) binding sites with
      11 bp spacing; overlap 11

<400> SEQUENCE: 2
tattctttgc tcaaaatttg atcaaatttt gagcaaagaa ta                     42

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence:paired
      Factor for Inversion Stimulation (Fis) binding sites with
      7 bp spacing; overlap 7

<400> SEQUENCE: 3
aggcttttgc tcaaagttta aactttgagc aaaagcct                          38

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence:sequence
      logo for Factor for Inversion Stimulation (Fis) binding
      site

<400> SEQUENCE: 4
gctcaaaatt tgatc                                                   15

<210> SEQ ID NO 5
<211> LENGTH: 58
<212> TYPE: DNA
<213> ORGANISM: Artificial Sequence
<220> FEATURE:
<223> OTHER INFORMATION: Description of Artificial Sequence:Factor for
      Inversion Stimulation (Fis) binding sites
      separated by 23 bp; separated 23

<400> SEQUENCE: 5
ggaattcttt gctcaaaatt tgatcaggat cctgatcaaa ttttgagcaa agaattcc    58
```

```
<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:18.1 bit
      Fis site

<400> SEQUENCE: 6
tttgctcaaa atttgatcaa a                                             21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:18.1 bit Fis
      site

<400> SEQUENCE: 7
tttgatcaaa ttttgagcaa a                                             21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:12.7 bit Fis
      site

<400> SEQUENCE: 8
tttgctcaaa gtttaaactt t                                             21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:12.7 bit Fis
      site

<400> SEQUENCE: 9
aaagtttaaa ctttgagcaa a                                             21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:15.0 bit Fis
      site

<400> SEQUENCE: 10
tttgctcaaa atttgatcag g                                             21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:15.0 bit Fis
      site

<400> SEQUENCE: 11
cctgatcaaa ttttgagcaa a                                             21
```

-continued

<210> SEQ ID NO 12
<211> LENGTH: 46
<212> TYPE: DNA
<213> ORGANISM: Escherichia coli
<220> FEATURE:
<223> OTHER INFORMATION: origin of replication (oriC)

<400> SEQUENCE: 12
gttatacaca actcaaaaac tgaacaacag ttgttctttg gataac        46

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence:Fis site
      separated by 11 bases; 9.1 bit Fis site

<400> SEQUENCE: 13
gaacaacagt tgttc        15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence:Fis site
      separated by 11 bases; 8.4 bit Fis site

<400> SEQUENCE: 14
actcaaaaac tgaac        15

<210> SEQ ID NO 15
<211> LENGTH: 113
<212> TYPE: DNA
<213> ORGANISM: Artificial Sequence
<220> FEATURE:
<223> OTHER INFORMATION: Description of Artificial Sequence:synthesized
      single very long nucleic acid with hairpin loop
      DNA

<400> SEQUENCE: 15
aacgggatcc actcaaaaac tgaacaacag ttgttcgaat tcctcgagcg atcggcgaag        60
ccgatcgctc gaggaattcg aacaactgtt gttcagtttt tgagtggatc ccg        113

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:8.4 bit Fis
      site

<400> SEQUENCE: 16
tccactcaaa aactgaacaa c        21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:10.0 bit Fis
      site

<400> SEQUENCE: 17
actgaacaac agttgttcga a        21

-continued

```
<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:10.0 bit Fis
      site

<400> SEQUENCE: 18
ttcgaacaac tgttgttcag t                                                21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:8.4 bit Fis
      site

<400> SEQUENCE: 19
gttgttcagt ttttgagtgg a                                                21
```